(12) United States Patent
Burdea

(10) Patent No.: US 9,028,258 B2
(45) Date of Patent: May 12, 2015

(54) COMBINED COGNITIVE AND PHYSICAL THERAPY

(75) Inventor: Grigore C. Burdea, Highland Park, NJ (US)

(73) Assignee: Bright Cloud International Corp., Highland Park, NJ (US)

( * ) Notice: Subject to any disclaimer, the term of this patent is extended or adjusted under 35 U.S.C. 154(b) by 633 days.

(21) Appl. No.: 12/942,668

(22) Filed: Nov. 9, 2010

(65) Prior Publication Data

US 2011/0112441 A1 May 12, 2011

Related U.S. Application Data

(63) Continuation-in-part of application No. 12/192,818, filed on Aug. 15, 2008.

(60) Provisional application No. 61/259,551, filed on Nov. 9, 2009, provisional application No. 60/964,861, filed on Aug. 15, 2007.

(51) Int. Cl.
*A63B 21/06* (2006.01)
*A63F 13/00* (2014.01)
(Continued)

(52) U.S. Cl.
CPC ............ *A63B 21/06* (2013.01); *G06F 19/3481* (2013.01); *G06F 19/3487* (2013.01);
(Continued)

(58) Field of Classification Search
CPC ............ G06F 19/3481; G06F 19/3487; G06F 19/003; A61B 5/002; A61B 5/11; A61B 5/0022; A61B 5/0024; A61B 5/0482; A61B 24/00; A61B 24/0059; A61B 24/0087; A61B 69/0057; A61H 2201/50; A61H 2201/163; A61H 1/00; A61H 1/0274; A61H 1/0277; A61H 1/0281; A61H 1/0285; A61H 2003/006; A61H 2205/06; A61F 5/3715; A61F 5/3723; A61F 5/373; A61F 13/00; A61F 19/24
USPC .......... 434/247, 258, 260, 261, 262; 600/595; 482/1, 4, 44–46, 49, 50; 128/869, 878, 128/920
See application file for complete search history.

(56) References Cited

U.S. PATENT DOCUMENTS 6,827,579 B2 * 12/2004 Burdea et al. ................. 434/258
7,138,976 B1 * 11/2006 Bouzit et al. .................. 345/156
(Continued)

FOREIGN PATENT DOCUMENTS

DE          3042682 A  *  6/1982     ............... A61H 1/00

OTHER PUBLICATIONS

English Machine Translation of DE 3042682 A.*
(Continued)

*Primary Examiner* — Nikolai A Gishnock
(74) *Attorney, Agent, or Firm* — Graham Curtin PA

(57) ABSTRACT

The present invention provides method and apparatus to perform combined cognitive and motor rehabilitation on a computerized non-portable system or on single portable device. A patient can play a variety of games that require the patient to perform a variety of memory exercises which involve physical exertion. The activities of the patient are monitored with pattern analysis software which provides feedback to the patient. The feedback can include voice synthesis, video guidance, progression messages etc. Patient data obtained while the patient is performing each of the memory exercises is stored locally on a database module and then uploaded to a cloud server. A remote psychologist/psychiatrist monitors the patient by logging into the same cloud, and updating cognition exercises. The same therapist can have live chats with the patient for further interaction and coaching.

10 Claims, 29 Drawing Sheets

(51) Int. Cl.

| | | |
|---|---|---|
| *G09B 19/00* | (2006.01) | |
| *A61B 5/04* | (2006.01) | |
| *A61B 5/22* | (2006.01) | |
| *A61H 1/02* | (2006.01) | |
| *A63B 69/00* | (2006.01) | |
| *A61B 5/11* | (2006.01) | |
| *A61B 5/0482* | (2006.01) | |
| *A63F 9/24* | (2006.01) | |
| *A63B 23/12* | (2006.01) | |
| *A63B 71/06* | (2006.01) | |
| *G06F 19/00* | (2011.01) | |
| *A61B 5/00* | (2006.01) | |
| *A61F 5/37* | (2006.01) | |
| *A63B 24/00* | (2006.01) | |
| *A63B 22/00* | (2006.01) | |
| *A63B 59/00* | (2006.01) | |

(52) U.S. Cl.
CPC ........... *G09B19/00* (2013.01); *A61B 5/002* (2013.01); *A61B 5/0022* (2013.01); *A61B 5/0024* (2013.01); *A61H 1/0274* (2013.01); *A61F 5/373* (2013.01); *A63B 69/0057* (2013.01); *A63B 24/0087* (2013.01); *A63F 13/00* (2013.01); *A61B 5/11* (2013.01); *A61B 5/0482* (2013.01); *A63F 9/24* (2013.01); *A63B 23/12* (2013.01); *A63B 24/0003* (2013.01); *A63B 24/0006* (2013.01); *A63B 24/0021* (2013.01); *A63B 24/0059* (2013.01); *A63B 24/0062* (2013.01); *A63B 71/0622* (2013.01); *A63B 2022/0092* (2013.01); *A63B 2024/0015* (2013.01); *A63B 2024/0096* (2013.01); *A63B 2059/0022* (2013.01); *A63B 2071/063* (2013.01); *A63B 2071/0647* (2013.01); *A63B 2071/065* (2013.01); *A63B 2071/0655* (2013.01); *A63B 2209/10* (2013.01); *A63B 2220/13* (2013.01); *A63B 2220/17* (2013.01); *A63B 2220/24* (2013.01); *A63B 2220/30* (2013.01); *A63B 2220/40* (2013.01); *A63B 2220/51* (2013.01); *A63B 2220/56* (2013.01); *A63B 2220/58* (2013.01); *A63B 2220/803* (2013.01); *A63B 2220/806* (2013.01); *A63B 2225/15* (2013.01); *A63B 2225/20* (2013.01); *A63B 2225/50* (2013.01); *G06F 19/3418* (2013.01); *Y10S 128/92* (2013.01)

(56) References Cited

U.S. PATENT DOCUMENTS

| | | | |
|---|---|---|---|
| 7,452,336 | B2 * | 11/2008 | Thompson .................... 600/558 |
| 7,856,264 | B2 * | 12/2010 | Firlik et al. ........................ 607/3 |
| 2002/0103429 | A1 * | 8/2002 | deCharms .................... 600/410 |
| 2002/0146672 | A1 * | 10/2002 | Burdea et al. ................. 434/258 |
| 2003/0120183 | A1 * | 6/2003 | Simmons ..................... 600/595 |
| 2005/0065452 | A1 * | 3/2005 | Thompson .................... 600/558 |
| 2005/0167907 | A1 * | 8/2005 | Curkendall et al. .......... 273/108 |
| 2005/0181347 | A1 * | 8/2005 | Barnes et al. ................. 434/350 |
| 2005/0216243 | A1 * | 9/2005 | Graham et al. ................. 703/11 |
| 2005/0283053 | A1 * | 12/2005 | deCharms .................... 600/300 |
| 2006/0161218 | A1 * | 7/2006 | Danilov .......................... 607/45 |
| 2006/0241718 | A1 * | 10/2006 | Tyler et al. ...................... 607/45 |
| 2007/0060445 | A1 * | 3/2007 | Reinkensmeyer et al. ....... 482/1 |
| 2007/0179534 | A1 * | 8/2007 | Firlik et al. ........................ 607/3 |
| 2007/0250119 | A1 * | 10/2007 | Tyler et al. ........................ 607/2 |
| 2008/0009772 | A1 * | 1/2008 | Tyler et al. ..................... 600/595 |
| 2009/0131225 | A1 * | 5/2009 | Burdea et al. ..................... 482/5 |
| 2012/0136274 | A1 * | 5/2012 | Burdea et al. ................. 600/545 |

OTHER PUBLICATIONS

Burdea, G. ; Rabin, Bryan ; Chaperon, Aurelien ; Hundal, Jasdeep. Emotive, cognitive and motor rehabilitation post severe traumatic brain injury—A new convergent approach Virtual Rehabilitation (ICVR), 2011 International Conference on (DOI: 10.1109/ICVR.2011.5971817) Publication Year: 2011 , pp. 1-8.*

Adamovich S. A Virtual Reality-Based Exercise System for Hand Rehabilitation Post-Stroke. Presence: Teleoperators & Virtual Environments [serial online]. Apr. 2005;14(2):161-174. Available from: Computer Source, Ipswich, MA. Accessed Dec. 15, 2014.*

* cited by examiner

COMBINED COGNITIVE AND PHYSICAL THERAPY

STATEMENT OF RELATED CASES

This application claims priority to provisional patent application Ser. No. 61/259,551 filed on Nov. 9, 2009, which is incorporated herein by reference.

This application is also a continuation-in-part of U.S. patent application Ser. No. 12/192,818, filed on Aug. 15, 2008, which claims the benefit of provisionally filed patent application Ser. No. 60/964,861, filed on Aug. 15, 2007, both of which are incorporated herein by reference.

BACKGROUND

Patients affected by stroke and other brain injury diseases develop cognitive impairments, such as memory loss or depression. Traditionally, therapy is done one-on-one with a psychologist (for cognitive therapy) and a physical and occupational therapist (for physical or occupational rehabilitation), requiring the disabled to travel to several offices or clinics. Since these patients are affected by motor impairments (difficulty moving limbs) travel to clinics/offices is difficult and costly.

However, since it is a single human body, and a single brain, certain interactions occur, with physical activity having a positive influence on cognition and well being (due to brain plasticity and the proximity of control regions in the brain) and vice versa. It is known in the art, for example that motor imagery (imagining motion of the affected limb) actually helps recovery of function for that limb. It is also known that physical activity, such as walking, helps delay the onset of Alzheimer's disease in the elderly.

Accordingly, new and improved methods and apparatus to provide cognitive and physical/occupational therapy, combined and simultaneously, particularly to patients suffering strokes, traumatic brain injury or brain diseases, are needed.

SUMMARY

The present invention provides method and apparatus to perform combined cognitive and motor rehabilitation on a computerized non-portable system or on single portable device. The portable device can be a cell phone, a laptop computer, a digital assistant, an iPad or any other portable device. In accordance with one aspect of the present invention, a patient performs a variety of memory exercises which also involve physical exertion. In one embodiment of the present invention, the patient performs the memory exercises in the form of games, which also involve moving the affected arm over its reach.

In accordance with another aspect of the present invention, pattern analysis software provides feedback to a patient. The feedback can include voice synthesis, interactive sounds, video guidance, progression messages, summary of scores, number of errors, etc. Patient data obtained while the patient is performing each of the memory exercises is stored locally on a database module, then uploaded to a cloud server.

A remote psychologist/psychiatrist monitors the patient by logging into the same cloud, monitoring results and updating cognition exercises. The same therapist can have live chats with the patient for further interaction and coaching.

The same computerized system or portable device is used in neuro-motor rehabilitation of the patient. Limb movements, head movements, or torso movements are measured by a plurality of device sensors. The device sensors can include a camera, accelerometers, goniometer, vision cameras and the like.

Thus, an aspect of the present invention provides cognitive and physical therapy that is combined, temporally and in one location. The therapy can be performed in the form of games. It also allows a therapist as well as the psychologist to be local or remote.

In accordance with one aspect of the present invention, a method of providing cognitive and physical rehabilitation to a patient with a computer is provided. The method includes a patient playing a virtual reality game operating on the computer, measuring cognitive responses of the patient by measuring results of the patient playing the software game, measuring motor responses of the patient with one or more devices while the patient plays the software game and reporting the motor response to the computer, and the computer reporting the measured cognitive response and the measured motor responses to a networked server that stores the measured cognitive response and the measured motor responses. First and second medical services providers can access the measured cognitive responses of the patient by accessing the server over the network. Additional medical service providers can also access the measured motor responses. These medical services providers can direct the patient in accordance with the instructions from the medical services providers provided on remote computers.

The measured cognitive responses can include measurements of reaction speed, short term memory, long term memory, pairing memory, focusing, and executive function. The measured motor responses can include strength, speed and motor coordination, limb range of motion, endurance (number of repetitions), movement smoothness, movement error versus a given ideal path.

The computer analyzes the cognitive responses and the measured motor responses and provides immediate feedback to the patient.

The measuring devices are connected to the computer and used by the patient. The measuring devices can be selected from the group consisting of: one or more cameras, one or more accelerometers, one or more weights, one or more dynamometers, one or more timers, one or more counters, one or more goniometers, one or more tilt tables, one or more pressure sensors and combinations thereof.

The network is preferably the Internet. A corresponding system is also provided by the present invention. It is appreciated that one or more remote servers can be used. Utilizing such a multitude of servers is known in the art as cloud computing. It is further claimed that utilizing such a cloud computing in rehabilitation will constitute a cloud rehabilitation method.

DESCRIPTION

Figure 1:
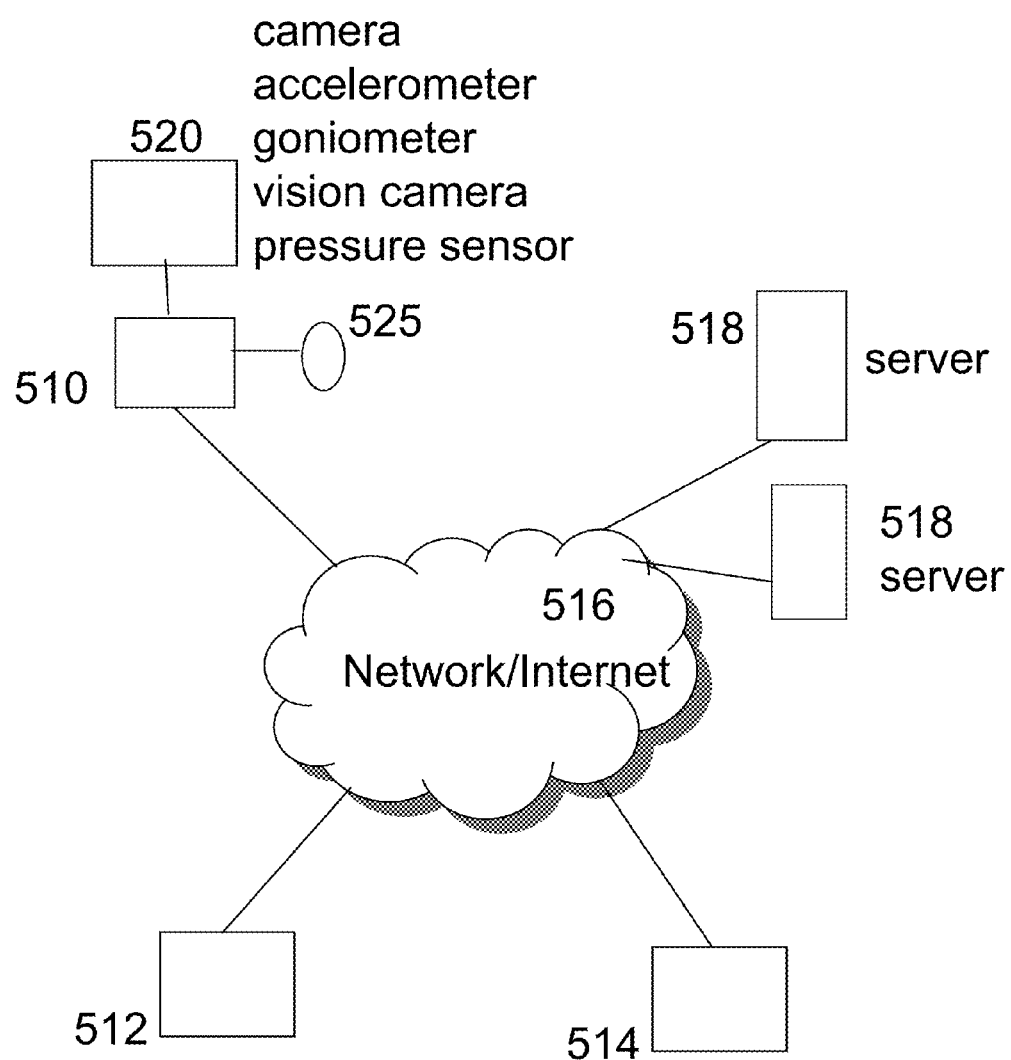
FIG. 1 illustrates a system in accordance with one aspect of the present invention.

In accordance with one aspect of the present invention, a combination of cognitive and motor rehabilitation on a computerized non-portable system or on single portable device is provided. The portable device may be a cell phone, laptop computer, iPad or the like. A patient performs a variety of memory exercises which also involve physical exertion. The physical exertion is different from that required to move a simple computer mouse. The patient performs all these in the form of games, which are executed on the computer device.

Pattern analysis software operating on the local computer provides feedback to patient. The feedback can include voice synthesis, video guidance, interactive sound, progression messages and the like. Patient data is stored locally on a database module, then uploaded to a cloud server. A remote psychologist/psychiatrist monitors the patient by logging into the same cloud, and updating cognition exercises. The same therapist can have live chats with the patient for further interaction and coaching. The same computerized system or portable device is used in neuro-motor rehabilitation of the patient. Limb movements are measured by the device sensors which includes but is not limited to camera, accelerometers, goniometer, pressure sensor, vision cameras etc, and used to play the combined cognitive/motor rehabilitation games in a convergent therapy session. The patient uses an input device 525 to perform the exercises. Such an input device can be a mouse, a joystick, a haptic device or any input device that is connected to a computer that can be applied by the patient to perform one or more exercise in accordance with an aspect of the present invention. A sensor 520 may be a part of an input device, it may also be separate from the input device. Input devices that provide mechanical resistance to movement are also known. The amount of resistance can be set or programmed.

Feedback on performance is provided to the patient through graphics, interactive sound, touch feedback (vibration), and other modalities. Similar to cognitive therapy, there is a rehabilitation coach software providing feedback to the patient. The same database module stores performance measures on patient limb movement and uploads them to the cloud servers. A physical or occupational therapist logs into the cloud and monitors patient, updates therapy and can have live chats.

In the portable/hand held device at the patient location there is an integration coach software 550. The Integration Coach 550 monitors the activities of the two software modules: cognitive coach and rehab coach software modules. The integration coach makes sure that the patient does not skip on either types of therapies and uses specialized software to determine correlations between improvements in one domain (cognition) vs. motor functional improvements. Such correlations are sent to both real therapists facilitating coordination/collaboration between them. Statistical mega data are stored in the cloud as basis for medical policy decision makers.

An example of combined therapy play for a short teem memory game and a pairing cognitive function: Patients use their affected limb to pick and place pairs of graphical (virtual) objects displayed on a screen, floor, or walls. In another embodiment patients select cards on an island, which are initially face down by moving their arm or their feet on an incline, or on the floor. This movement is tracked and coupled with that of a hand or foot avatar in the game. Grasp forces may be sensed to determine selection (similar to clicking on a mouse but requiring multi-finger force exertion).

In accordance with various aspects of the present invention, therapy is combined, temporally and in one location, combined cognitive and physical therapy is provided in the form of games, patients play with the games by moving the affected arm or limb against resistance or with assistance and medical services providers (therapists and psychologists, for example) can be local or remote. It is also envisioned that patients may move two arms at a time, in the process of playing the therapeutic games. In such an embodiment, the game will use a plurality of portable or computer devices, and incorporate input from either limb, or from both simultaneously. The system of the present invention can also use two cameras, one camera to monitor movement of a first limb and a second camera to monitor movement of a second limb.

FIG. 1 illustrates a block diagram of the present invention. A local computer 510, a first remote computer 512 and a second remote computer 514 are connected to a network 516, such as the Internet. All computers have access, which can be password protected, to a server 518. It is appreciated that server 518 may in fact be a multitude of co-located servers. Measuring devices 520 are connected to the computer 510.

In accordance with one aspect of the present invention, a patient wears one or more of the measuring devices and plays a computer game running on the computer 510. It is understood that such measuring devices can be, for example, those embedded in cell phones. The computer game directs the patient to perform various motor functions and the measuring devices measure the response of the patient. The computer 510 also has analytical software that measures the patient's responses. The measuring devices send the measurements to the computer 510. The computer 510 stores the responses. After analyzing the responses, the computer 510 provides feedback to the patient. The computer 510 also sends the measured responses to the server(s) 518. It is also envisioned that in one embodiment, the measuring device (or devices) is located inside the cell phone.

Medical services providers on the computers 512 and 514 can log into the server(s) 518 via the network to access measured response data for a designated patient. For example, a first medical services provider uses the second computer to access the measured cognitive responses of the patient by accessing the server over the network and a second medical services provider uses the third computer to access the measured motor responses of the patient by accessing the server over the network. By way of example only, the first medical services provider may be a psychologist and the second medical services provider may be a physical therapist or occupational therapist. Additional medical service providers and additional remote computers may be added to the system. The medical services providers can provide instructions to the computer 510 over the network and through the server based on the measured cognitive and motor responses. The computer 510 can provide new instructions to the patient based on the instructions from the first and second medical services providers.

The measured cognitive responses include measurements of reaction speed, short term memory, long term memory, pairing memory, focusing and executive function. The measured motor responses include strength, speed, accuracy of path, tremor, accuracy of placement, limb endurance, motor coordination, range of movement The following are examples of physical parameters and how they can be measured and/or quantified:
speed of movement (camera or accelerometers);
range of movement (camera);

smoothness of movement (camera and accelerometer);
shoulder strength (wrist calibrated weights);
grip strength (dynamometer, pinchmeter and pressure sensor);
endurance of movement=distance moved (timer and counter);
score (game-dependent);
errors (game-dependent);

The following are examples of cognitive parameters and how they can be measured and/or quantified:
score (game-dependent);
errors (game-dependent);
short-term visual memory (errors in matching cards on Card Island game, time taken to match all);
executive function (errors in stacking disks in Tower of Hanoi 3D game, completion time); focusing (balls lost in Breakout 3D game vs. ball speed);
dual-tasking (game-dependent example move a ball grasped by the avatar by squeezing above a threshold, and maintaining an ideal path indicated in the game, else the ball drops).

As mentioned previously, the computer 510 includes software that analyzes the cognitive responses and the measured motor responses and provides feedback to the patient.

The one or more measuring devices can include one or more cameras, one or more accelerometers, one or more weights, one or more dynamometers, one or more timers, one or more counters, one or more goniometers, one or more tilt tables, one or more pressure sensors and combinations thereof.

Figure 2:
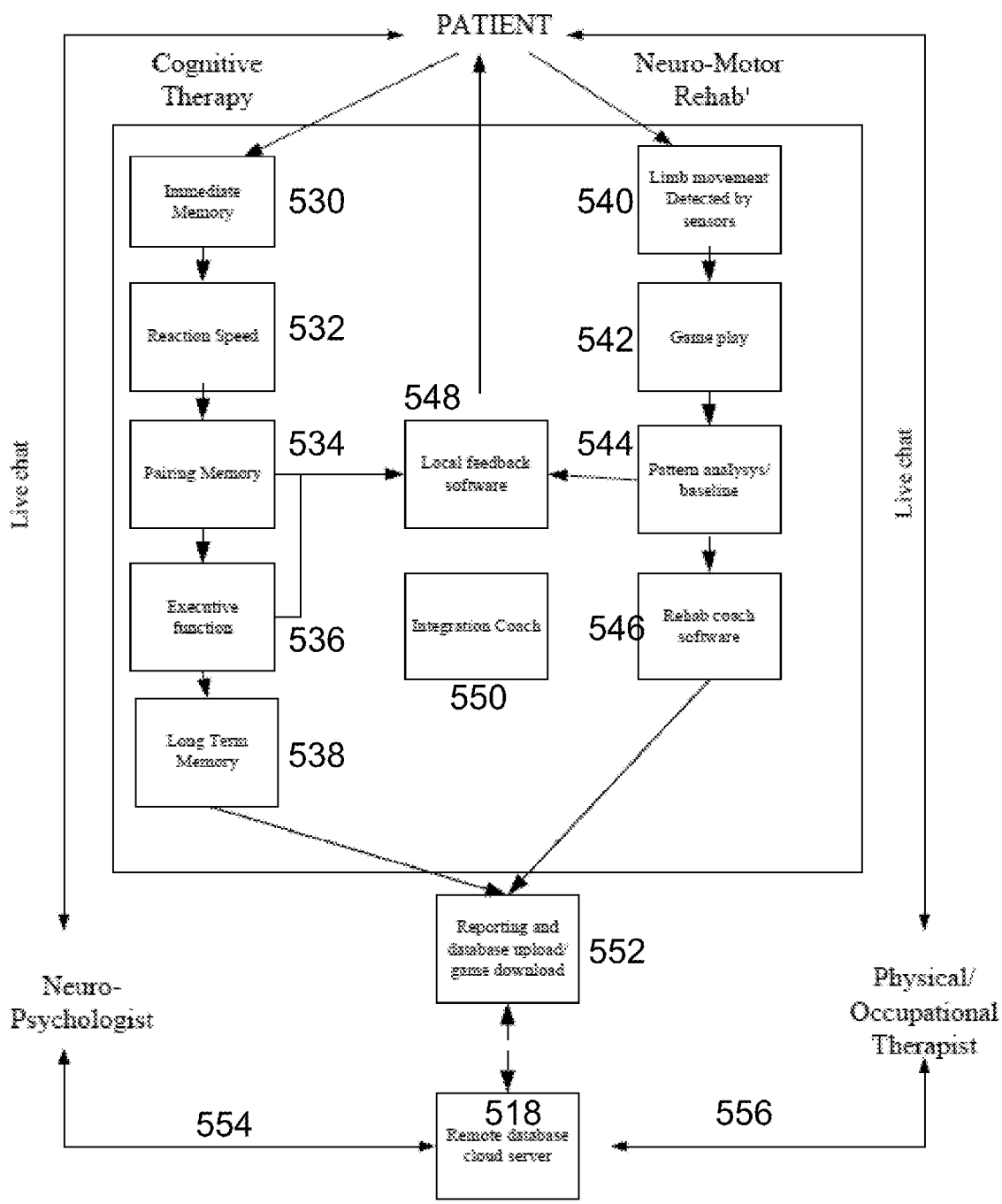
FIG. 2 illustrates a method in accordance with one aspect of the present invention.

FIG. 2 illustrates a method in accordance with an aspect of the present invention. A patient plays a game on the computer 510. The game provides cognitive therapy and motor skill therapy to the patent. One or more devices measure cognitive responses and motor responses. In step 530, the immediate (short-term) memory is measured. A Patient is requested to pair objects by shape, color, image. Some of the images are temporarily masked and patient needs to remember where they were in order to successfully pair.

In step 532, reaction speed is measured. A Patient is asked to perform an action as soon as an event occurs in the game. The shorter the time delay between the event and patient reaction, the higher the reaction speed.

In step 534, pairing memory is measured. It is understood that pairing memory is a component of short-term memory.

In step 536, executive function is measured. Executive function implies correct decisions made by patient to solve the problem posed in the game. The logic of patient's actions is measured through the number of errors incurred in the game, with the lower number of errors representing better executive function.

In step 538, long term memory is measured. Long term memory implies a patient remembering things that happened in the not immediate past. For example patient has to remember a pattern that was observed a few games prior, in order to solve the question posed in the current game. Again the number of errors made in the patient's actions and the completion time in solving it give a measure of long-term memory.

On the motor skills side, in step 540, limb movement is detected. This can be done with any type of known device. For example, the tilt table disclosed below can be used. Strength training is done by placing wrist or ankle weights on the patient limb extremity and asking the patient to play the games while wearing these weights.

In step 542, various parameters related to game play are measured. Parameters are scores, errors, velocities, path error vs. ideal path given.

In step 544, pattern analysis is performed. Pattern analysis software looks at game play history for a given patient. Game results provide input to the pattern analysis software, which also gets input from patient medical history and prior results at a game or combination of games. Repeated errors or game losses may lead to changes in the game difficulty. Patient that knows how to solve a cognitive problem, but cannot move the affected limb to do it, will lead the pattern analysis software to send information to the rehab coach to reduce the difficulty of the motor component of the game (reduce table tilt, for example), or to assist the patient in the motor component, by tilting the table the opposite way.

In step 546, rehab coach software, according to the session number or from a remote clinician, sequences the exercises according to the treatment prescribed, and changes the exercise difficulty based on input from pattern analysis software or from remote clinician. All of the responses are measured and stored on local memory in the local computer 510.

In step 548, software on the computer 510 analyzes the measured responses and provides feedback to the patient. The feedback can be provided using voice synthesis, interactive sounds, text messages, graphical message changes in the game scene, and the like.

In step 550, an integration coach measures the patient's responses to make sure that the patient is completing all aspects of the rehabilitation program. If the patient has difficulty with a given game the coach lowers the difficulty automatically, or substitutes the game with a similar one.

In step 552, the measured responses are provided to the server over the Internet. In steps 554 and 556, the medical service providers can access the measured responses for a selected patient and provide further feedback and instructions to the patient.

Any software game that requires a patient to exercise motor and cognitive skills can be used in the present invention. This includes specially designed software that requires a patient to use motor and cognitive skills in combination. An example of a game that can be used in the Tower of Hanoi 3D.

Figure 3:
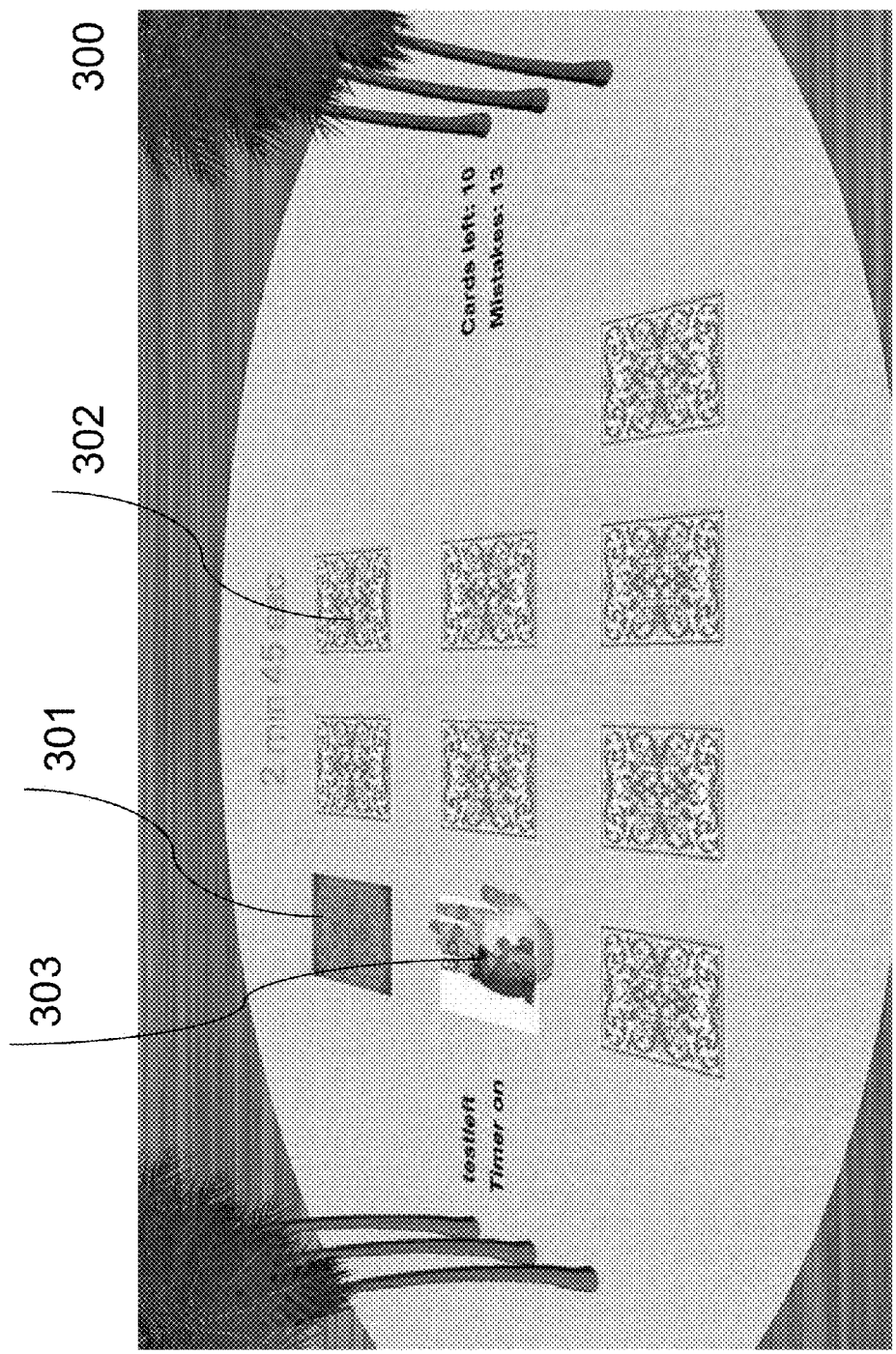
FIGS. 3 to 5 illustrate various games that can be used in accordance with an aspect of the present invention.
Figure 4:
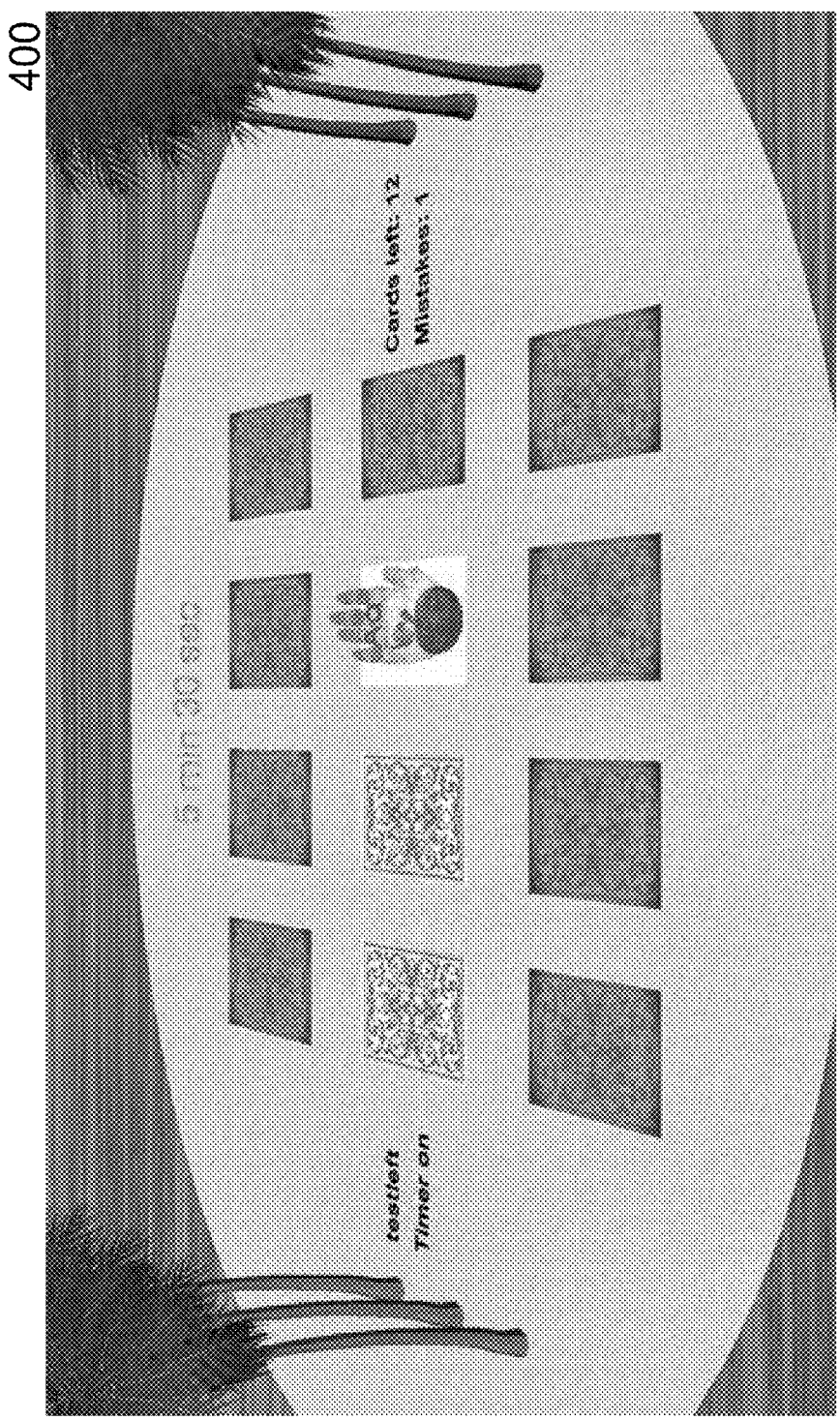
Figure 5:
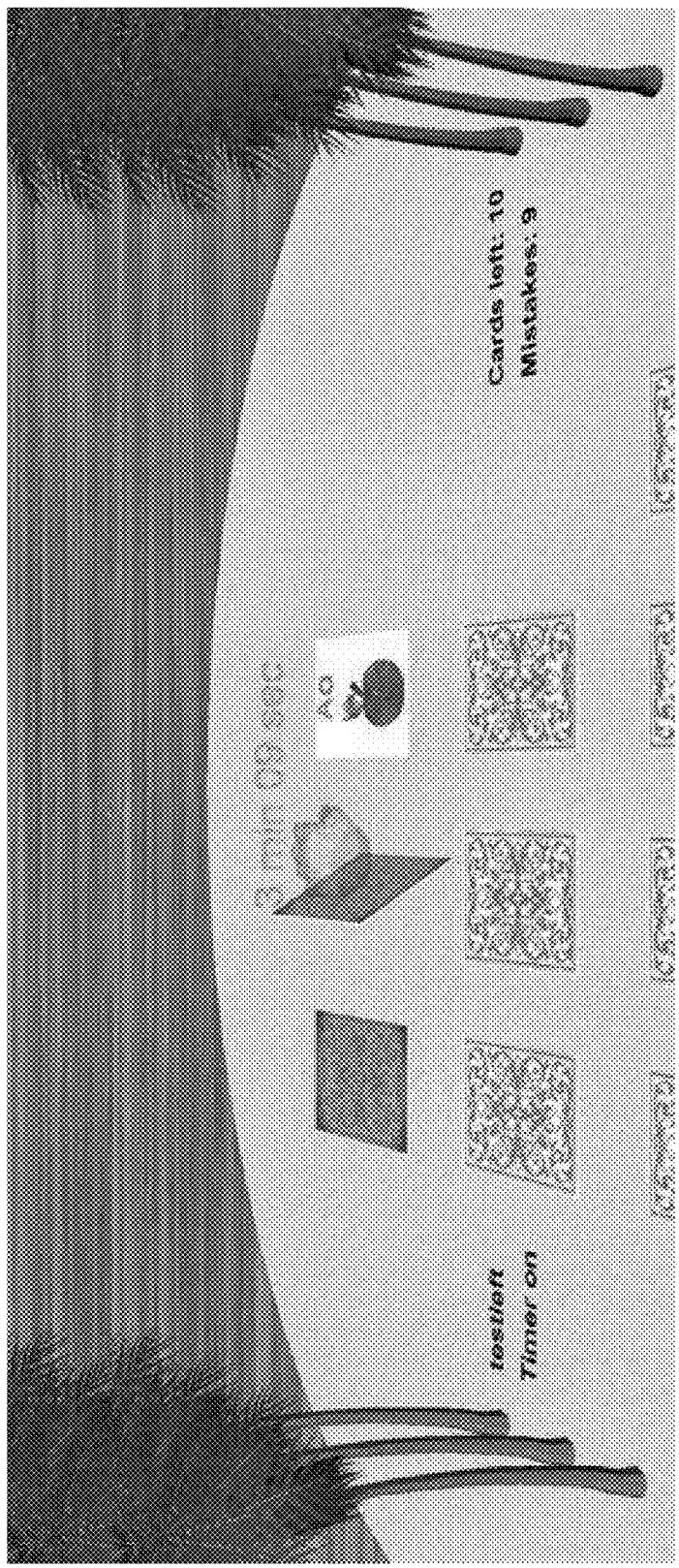

FIGS. 3-5 illustrate three screen images of a therapeutic game called the "Card Island." This is a card matching game used in short term visual memory training. FIG. 3 shows a screenshot 300 with cards. Cards that were never seen (never turned face up) are dark (301). Those that have been previously seen are with the white-grey design, such as 302. Hand avatar 303 is controlled by patient and the patient squeezes deformable element 44 in forearm support 25 when avatar 303 overlaps card to turn it face up. Avatar is then made transparent, so that patient can see under the hand. FIG. 4 shows a screenshot 400 "Card Island after 1 mistake." Herein, two cards have been mismatched, and turned back face down. Player is starting a new pairing action. The other cards have never been seen thus they are dark. Number of mistakes is displayed in the scene, as well as number of cards left. When cards are correctly paired they fly off the island.

FIG. 5 in screenshot 500 shows "Avatar grasping card" and shows the patient in the process of turning a card face up by for instance grasping a rubber ball interface 44 (not shown).

Figure 6:
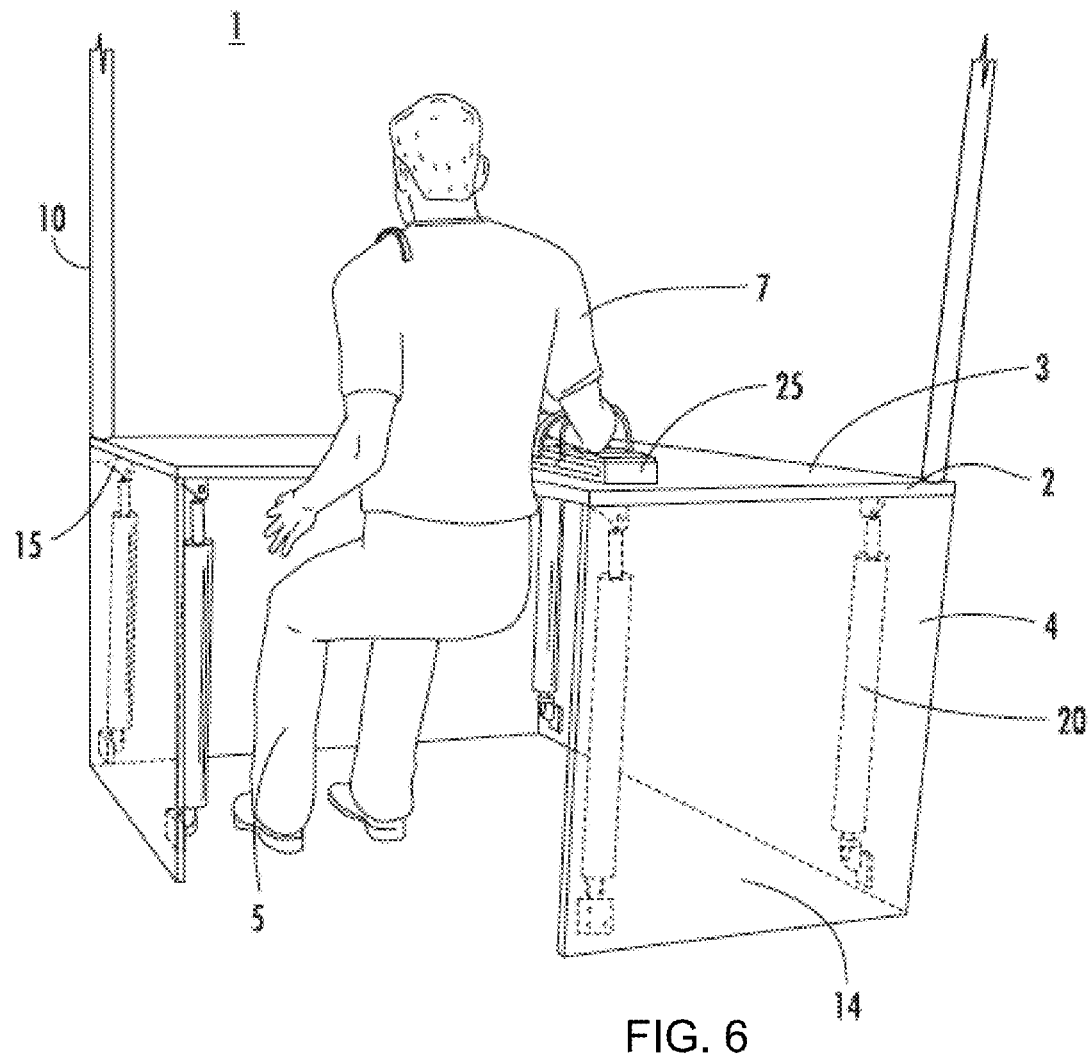
FIGS. 6 to 19, 20A to C, 21A to B and 22 illustrate apparatus and methods useful in accordance with various aspects of the present invention.
Figure 7:
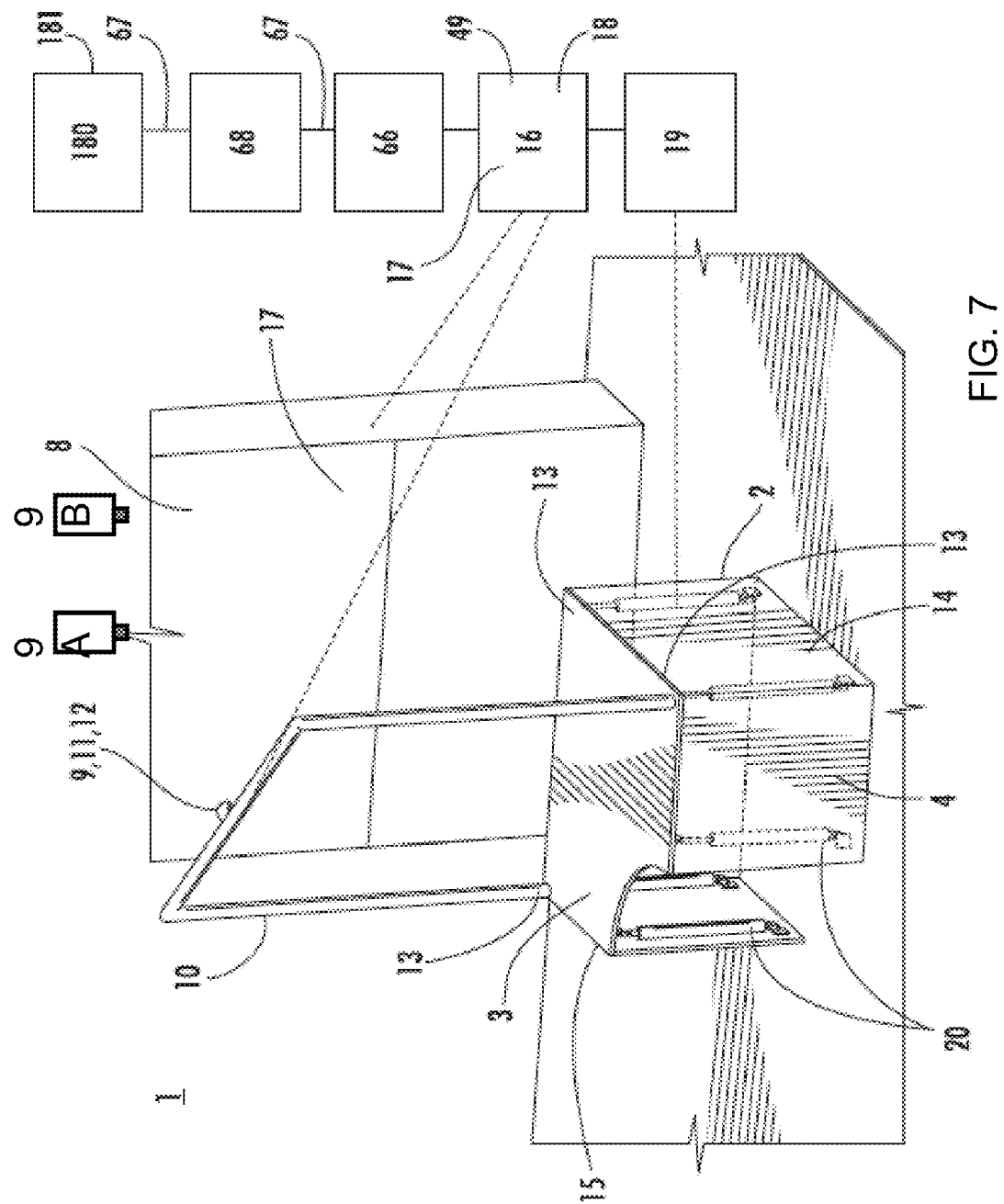

FIGS. 6 and 7 illustrate tilting rehabilitation table system 1. Tilting rehabilitation table system 1 incorporates tilting table 2 which has top surface 3 and underside surface 4. Top surface 3 can be a U-shaped, symmetrical, low-friction surface. Underside surface 4 can have a U-shape. For example, low top surface 3 can be made of carbon fiber, or other durable and light material, covered by a low-friction coating. Suitable low-friction coatings include TEFLON® sheets. Underside walls 14 extend upwardly from underside surface 4.

Patient 5 sits in chair 6 and rests arm 7 to be rehabilitated in low-friction forearm support 25. Patient 5 exercises while watching display 8 placed at the opposite side of tilting table 2. Preferably, display 8 is a large display such as a 55 inch diagonal TV. A video camera 9 is attached to ceiling in one embodiment. A video camera in another embodiment may also be attached to a wall or a structure. In yet a further embodiment a plurality of cameras is used, for instance two cameras 9A and 9B as illustrated in FIG. 7. This enables each arm of the patient to be tracked by an individual camera. This arrangement as shown in FIG. 7 allows video camera 9 or cameras 9A and 9B to view tilting table 2 and patient 5 simultaneously. Video camera 9 can be a conventional digital camera. Infrared filter 11 can be attached to lens 12 of video camera 9. LEDs 13 are mounted at the corners of top surface 3 and can be wired to direct current source (not shown). For example, LEDs can be used for providing calibration of video camera 9.

Computer 16 renders exercise simulation 17 and displays them on display 8. For example, exercise simulation 17 can be an animated or virtual reality sequence. Computer 16 is preferably a multi-core PC workstation. Computer 16 also receives input from video camera 9. Computer 16 runs tracking software 18 and communicates with controller 19. Controller 19 activates actuators 20 to provide tilt of top surface 3. Computer 16 is connected to Internet 66 and transparently uploads clinical data 67 to remote clinical database server 68. Remote computer 181 connected to clinical database server 68 over Internet 66 is used to execute remote graphing software 180.

Figure 8:
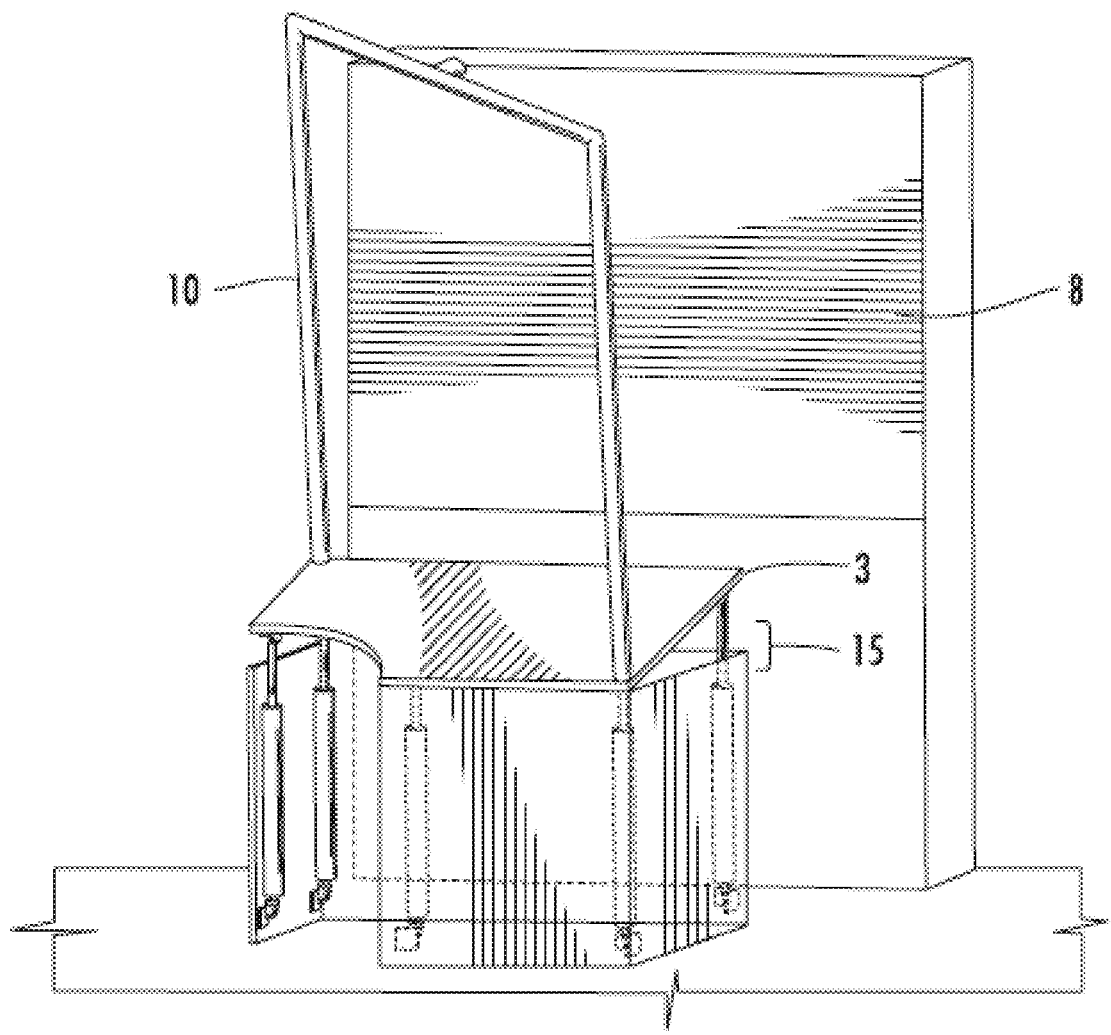

FIG. 8 shows the orientation of top surface 3 and camera support 10 when tilt angle 15 is increased to move the angle away from patient 5. Increased tilt angle 15 makes in/out movements of arm 7 more difficult. Further difficulty is increased by placing weights on patient's forearm support 25.

Figure 9:
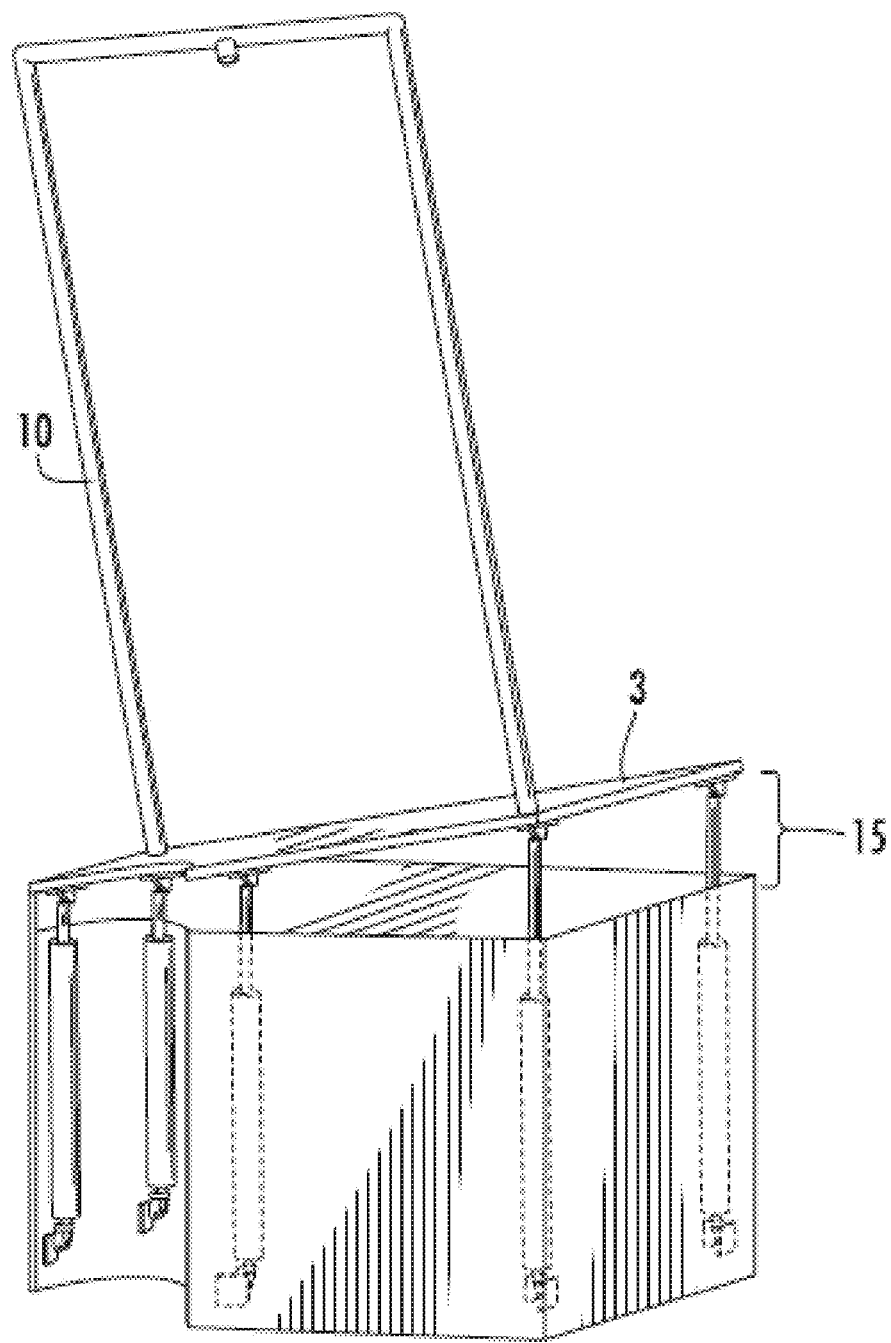

FIG. 9 shows a different tilt of top surface 3, in which tilt angle 15 is to the right of patient 5. This tilt angle makes arm movements from left-to-right more difficult than those when top surface 3 is horizontal. Other tilt angles 15 can be used when the left side of top surface 3 is tilted up or when the side closer to patient 5 is tilted up. These make more difficult corresponding arm 7 movements, such as right-left or out-in, respectively. In one embodiment, top surface 3 can be tilted in four degrees of freedom.

Figure 10:
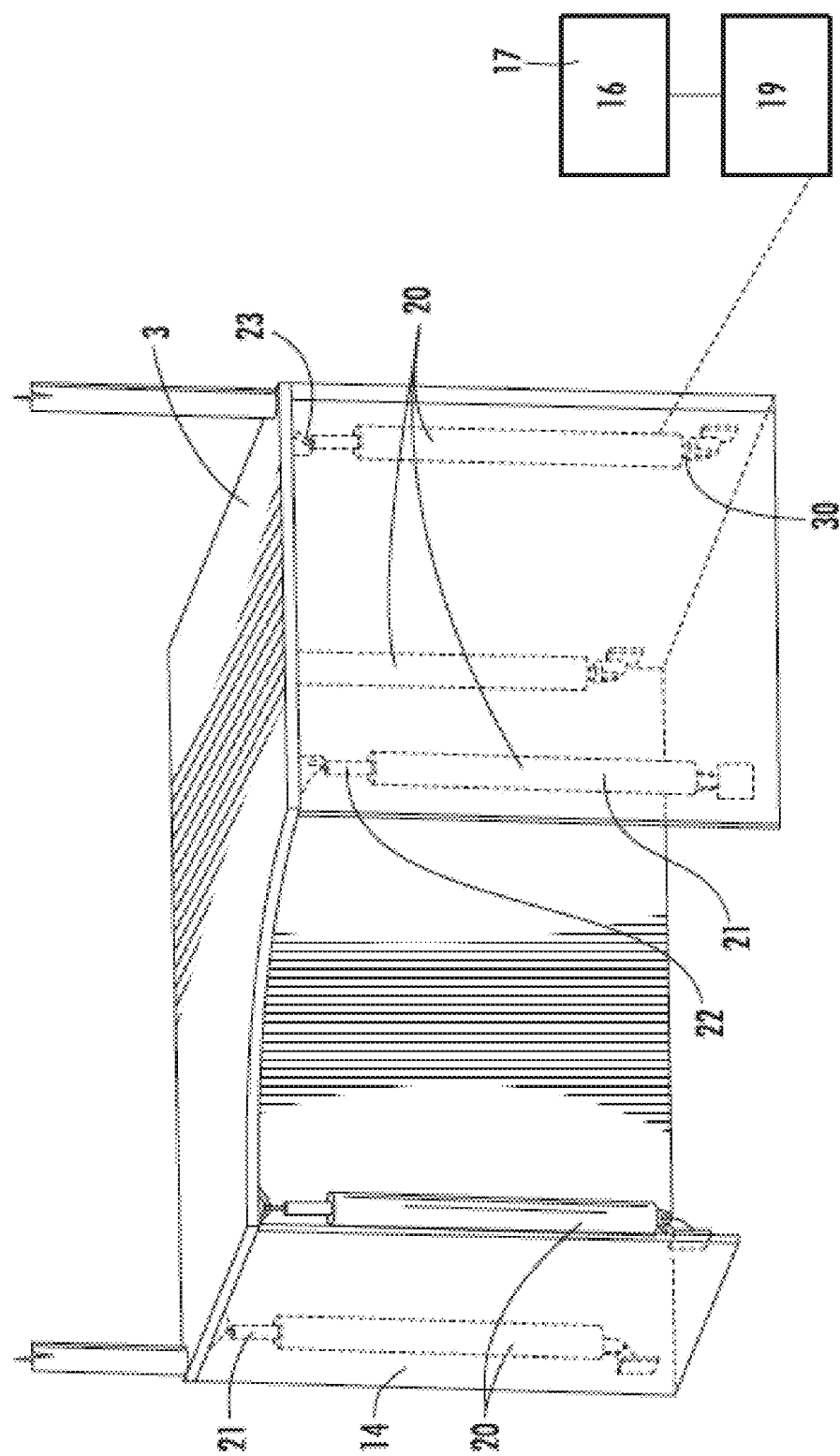

Tilt angle 15 is produced by two or more actuators 20 placed under top surface 3, as shown in FIG. 10. Actuators 20 are preferably linear electrical actuators. Actuators 20 are positioned under top surface 3. Each actuator 20 includes base 21 and translating shaft 22. Translating shaft 22 is connected to top surface 3 by top joint assembly 23. Base 21 is connected to underside walls 14 with bottom joint assembly 30. Actuators 20 are controlled by controller 19. Controller 19 can be a multi-channel micro-controller such as those which are available commercially. Controller 19 in turn receives commands from computer 16 running exercise simulation 17. In one embodiment, five actuators 20 can be used and the amount of translation of actuator shaft 22 provides tilt angle 15 which can be varied from about 0 degrees (horizontal) to about 30 degrees. The more top surface 3 is tilted, the larger the effect gravity has due to the weight of arm 7 of patient 5 and of forearm support 25 and the harder therapeutic exercise simulation 17 is to perform.

Figure 11:
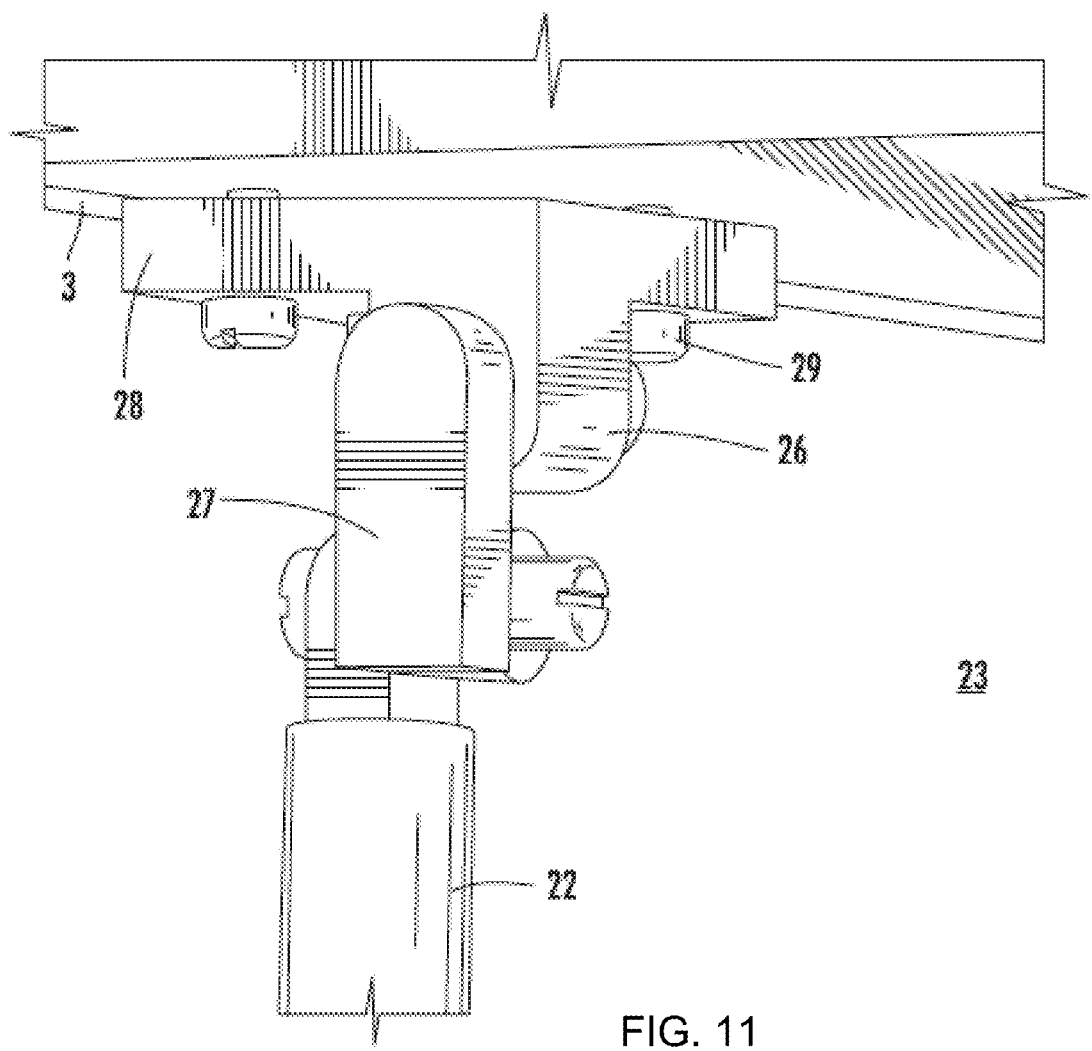

FIG. 11 shows a detailed view of top joint assembly 23 which connects actuator shaft 22 to the underside of top surface 3. Top joint assembly 23 has horizontal rotating joint 26 and vertical rotating joint 27 which together produce two degrees of freedom for top joint assembly 23. The axis of rotation of horizontal rotating joint 26 is perpendicular to the axis of rotation of vertical rotating joint 27. Horizontal rotating joint 26 is attached to the underside of top surface 3 using plate 28 and bolts 29.

Figure 12:
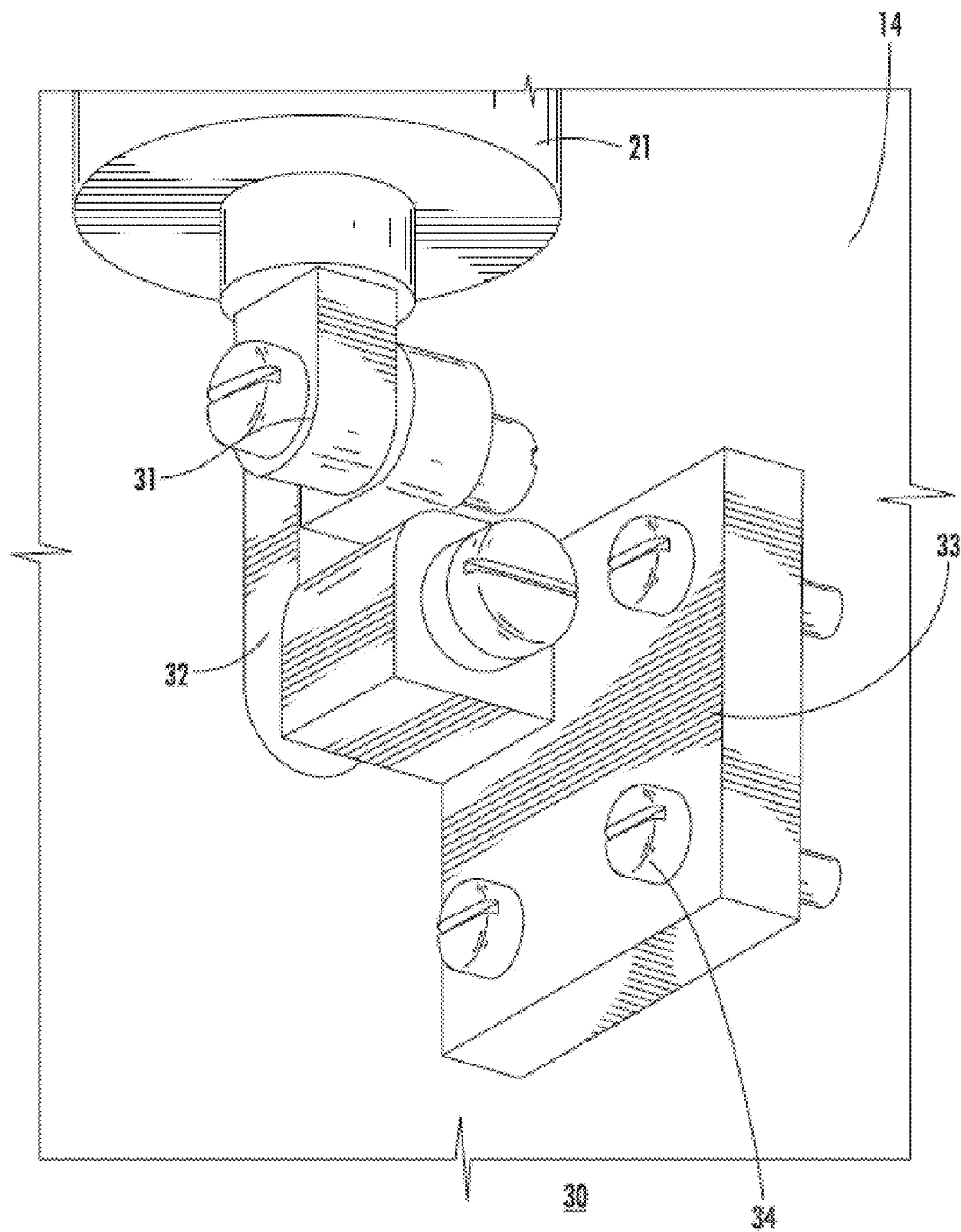

FIG. 12 shows a detailed view of bottom joint assembly 30, which connects base 21 to the inner side of underside walls 14. Bottom joint assembly 30 has horizontal rotating joint 31 and vertical rotating joint 32 which together produce two degrees of freedom for bottom joint assembly 30. The axis of rotation of horizontal rotating joint 31 is perpendicular to the axis of rotation of vertical rotating joint 32. Vertical rotating joint 32 is attached to the inner side of underside walls 14 through plate 33 and bolts 34.

Figure 13:
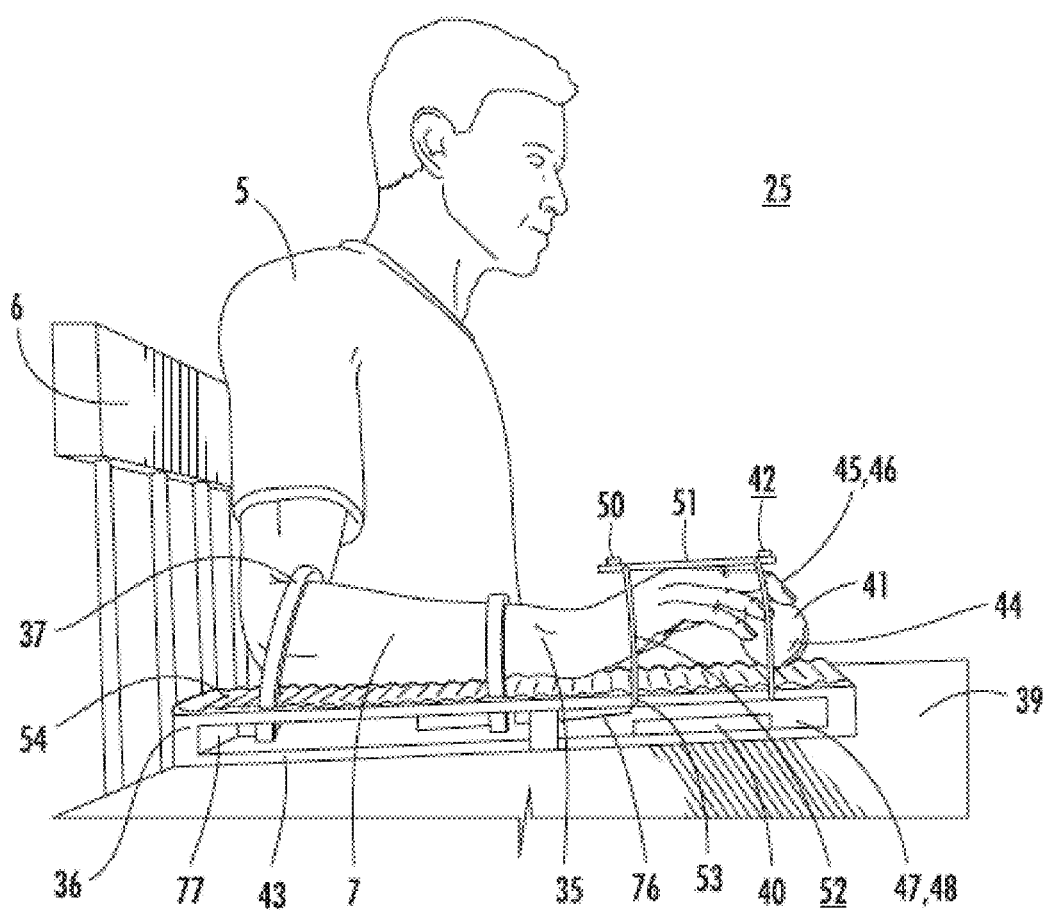
Figure 25:
FIGS. 25 and 26 illustrate a tilt table in accordance with an aspect of the present invention.

A side view of the patient 5 sitting in chair 6 and using of forearm support assembly 25 used by patient 5 is shown in FIG. 13. Forearm 7 and wrist 35 of patient 5 are secured to forearm support base 36 using a plurality of straps 37. For example, straps 37 can be formed of a hook and loop material of VELCRO®. Forearm support base 36 can be made of a lightweight material such as plastic, and is hollow. Pressure sensor 41 measures the air pressure inside hollow compliant element 44. A suitable hollow compliant element 44 can be a rubber ball. Grasping forces 45 exercised by fingers 46 of patient 5 are measured. Video camera 9 shown in FIG. 1 views LED assembly 42 which is formed of two infrared LEDs 50 mounted on plastic support 51 for providing data on arm movements and rotation. LED assembly 42 in turn is mounted on movable assembly 52. In another embodiment, LEDs can be placed at the tip of vertical poles 1300 attached to the forearm support 2503 to one of its side (as seen in FIG. 25). Movable assembly 52 rotates on hinges 53 attached to forearm support base 36. Movable assembly 52 rotates open to allow forearm 7 to be placed on forearm support top surface 54. Forearm support top surface 54 is preferably made of a compliant material (such as plastic foam), for increased comfort. It is envisioned that compliant plastic foam can be attached to top surface of forearm support by Velcro®. This allows compliant pad to be removed and replaced for each patient, so as to increase hygiene and minimize disease transmission. Forearm support base 36 has chambers 39, 76 and 77. Chamber 39 can be used to incorporate electronics assembly 40 to which is connected pressure sensor 41. Output of pressure sensor 41 is processed by electronics assembly 40. Electronics assembly 40 includes an analog-to-digital converter 47 and wireless transmitter 48. Transmitter 48 can be a conventional wireless Bluetooth® type transmitter. Transmitter 48 communicates with receiver 49 incorporated in computer 16, as shown in FIG. 7. Computer 16 can change exercise simulation 17 according to grasping forces 45 of patient 5. Computer 16 can also change exercise simulation 17 based on forearm 7 position/orientation given by video camera 9. For example, exercise simulation 17 can be rehabilitation games. LED assembly 42 and electronics assembly 40 are connected to battery 43 in chamber 77. Chamber 76 of base 36 can be used to allow the addition of modular weights 56. The addition of modular weights 56 to forearm support base 36 allows an increased difficulty of exercise simulation 17. The difficulty of performing exercise simulation 17 is increased with the increase in modular weights 56, with the increase in tilting angle 15, and with the number and level of exercise simulation 17.

Figure 14:
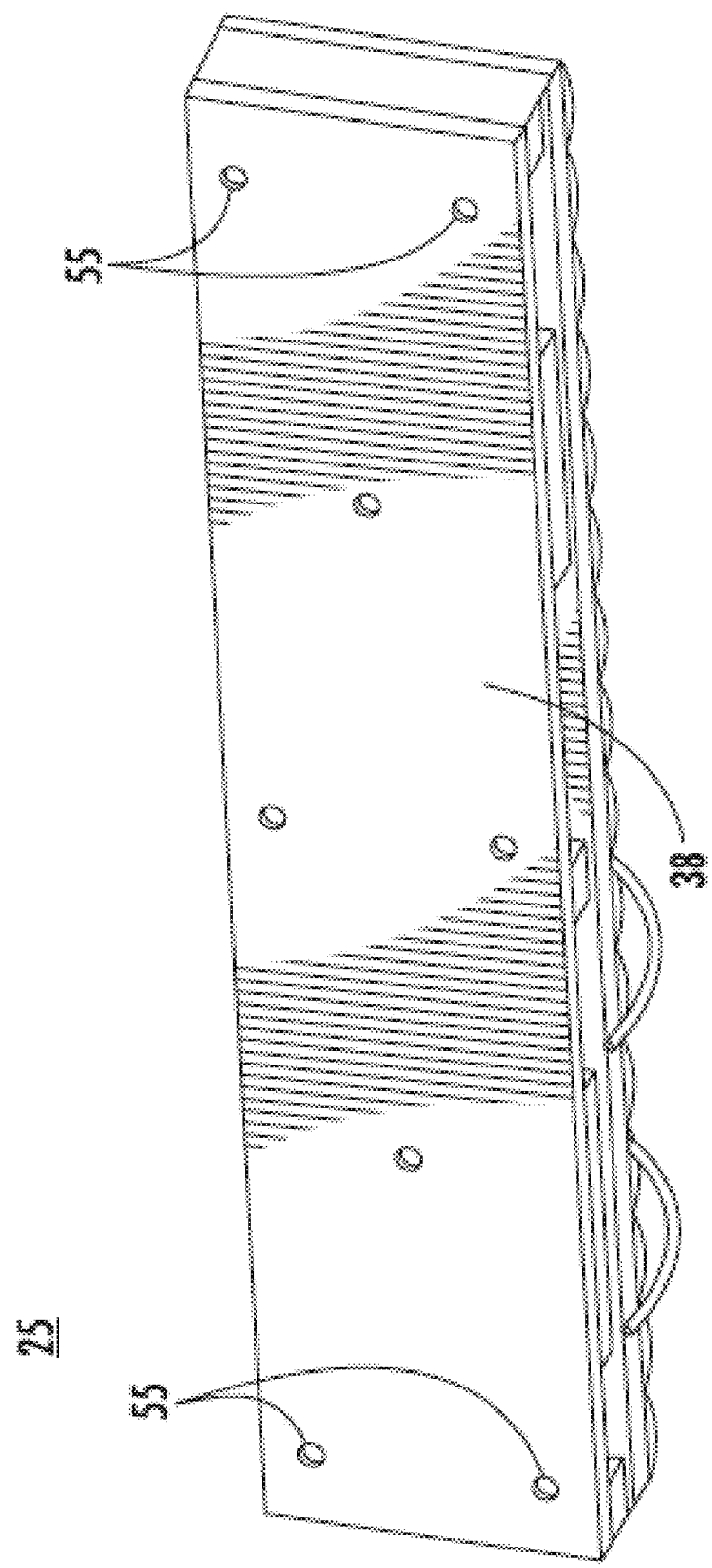

FIG. 14 is a view of the underside of the forearm support assembly 25. Underside surface 38 of forearm support 25 has a plurality of low friction studs 55. Low friction studs 55 are preferably made of TEFLON®.

Figure 15:
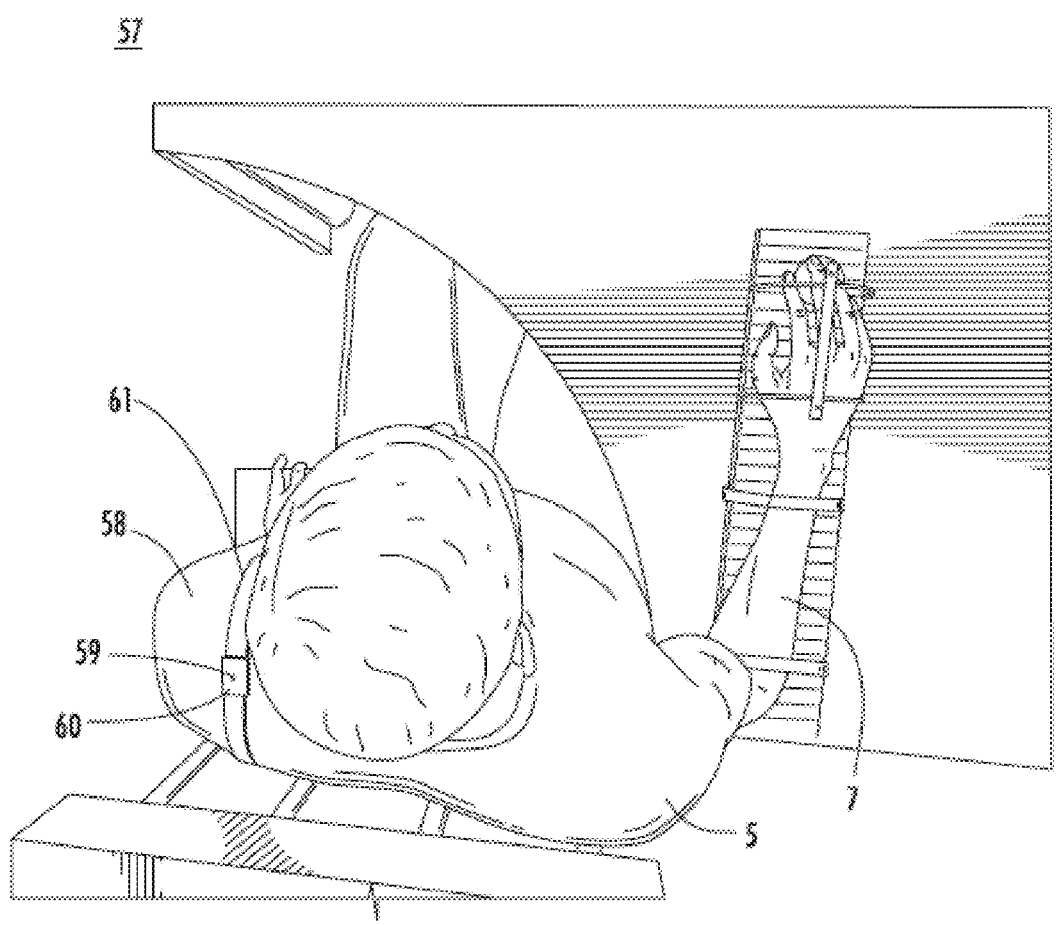

FIG. 15 shows shoulder harness assembly 57 worn by patient 5 on shoulder 58 opposite to arm 7 being rehabilitated.

Shoulder harness assembly 57 incorporates shoulder LED 59 wired to battery 60. Shoulder LED 59 is an infrared LED for providing data on compensatory movements of patient 5. Harness assembly 57 is formed of adjustable segments 61. Segments 61 are preferably formed of a hook and loop material, such as VELCRO®. Video camera 9 takes images of shoulder LED 59. Tracking software 18 running on computer 16 determines when patient 5 is doing undesirable compensatory leaning movements. Tracking software 18 can be adjusted by a therapist to be more sensitive, or less sensitive to leaning of patient 5. In another embodiment the shoulder harness is attached to a magnetic assembly, with one disk under the patient's garment and one on top. The magnetic force presses on the shoulder garment, keeping the shoulder harness in place.

Figure 16:
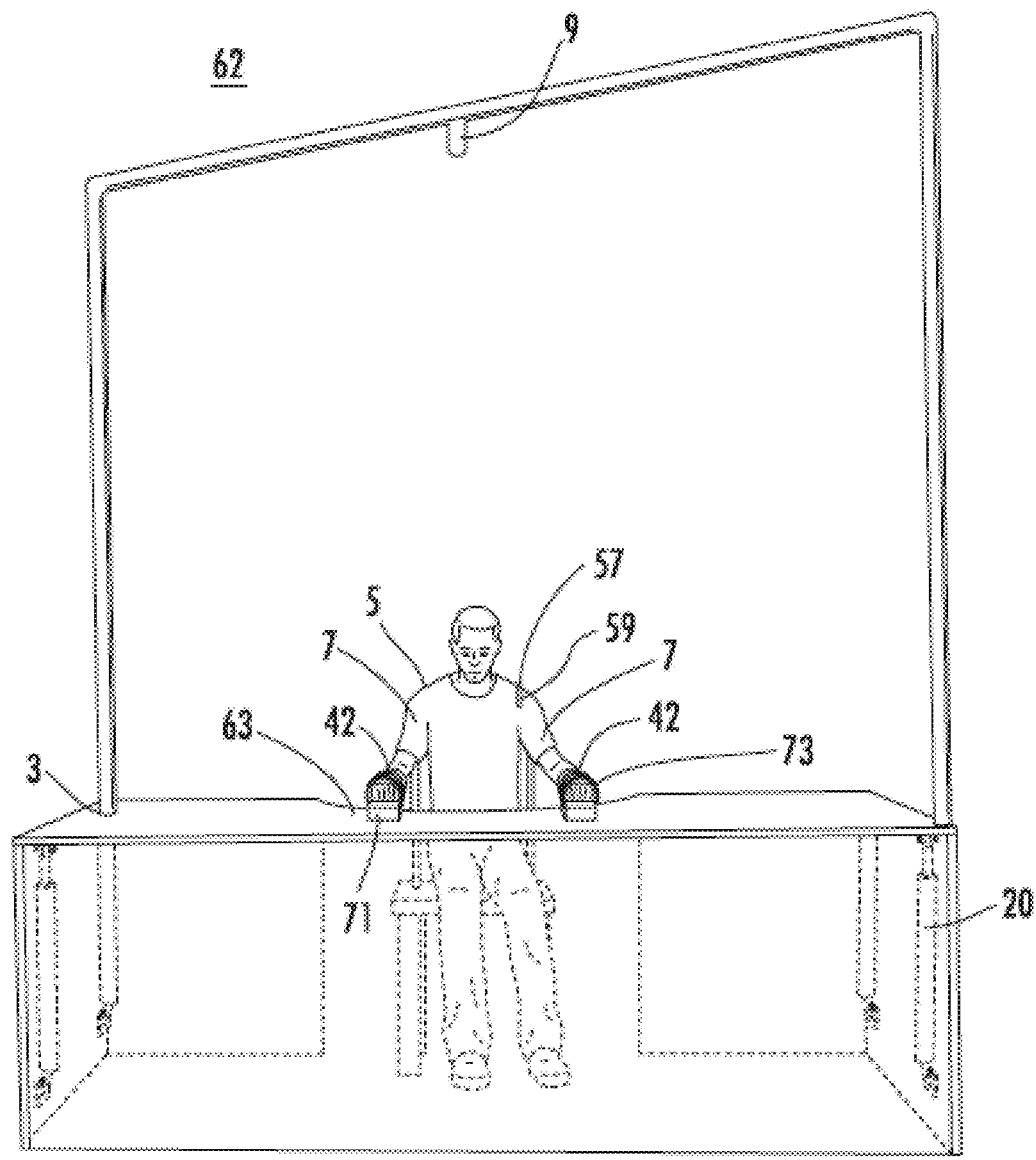

FIG. 16 illustrates an alternate embodiment of tilting table 62 for use with two forearm supports 25. Top surface 3 has a U-shape cutout 63 allowing patient 5 to be seated centrally to table axis 64. Patient 5 moves two arms 7 while supported by two low-friction forearm support assemblies 25. This allows training of both arms simultaneously, with benefits to recovery of patient 5. In one embodiment, patient 5 also wears one shoulder harnesses 57, as it is sufficient to detect the leaning of the shoulder opposite to the disabled arm 7. Video camera 9 views LEDs 42 on both forearm support assemblies 25, as well as LEDs 59 on one shoulder harness assembly 57. Forearm support assembly 25 is modified such that the number of infrared LEDs 42 differ between the two forearm support assemblies 25. For example three LEDs 42 will be on the left-arm forearm support 73, while the right-arm support 71 still has two LEDs 42 as previously described in FIG. 13. This allows tracking software 18 to differentiate between left arm and right arm movements. Tracking software 18 tracks two arms 7 in real time. Data from tracking software 18 is used by computer 16 to run two-arm exercise simulation 17. In this embodiment, the same type of actuators 20 as shown in FIG. 10, can be used in this embodiment. Preferably, four actuators 20 are used in this embodiment. It is envisioned that two cameras mounted on the ceiling could be used required to view the whole top of the table, as needed in dual arm exercises. In such an arrangement each camera will roughly view more than half of the table.

Figure 17:
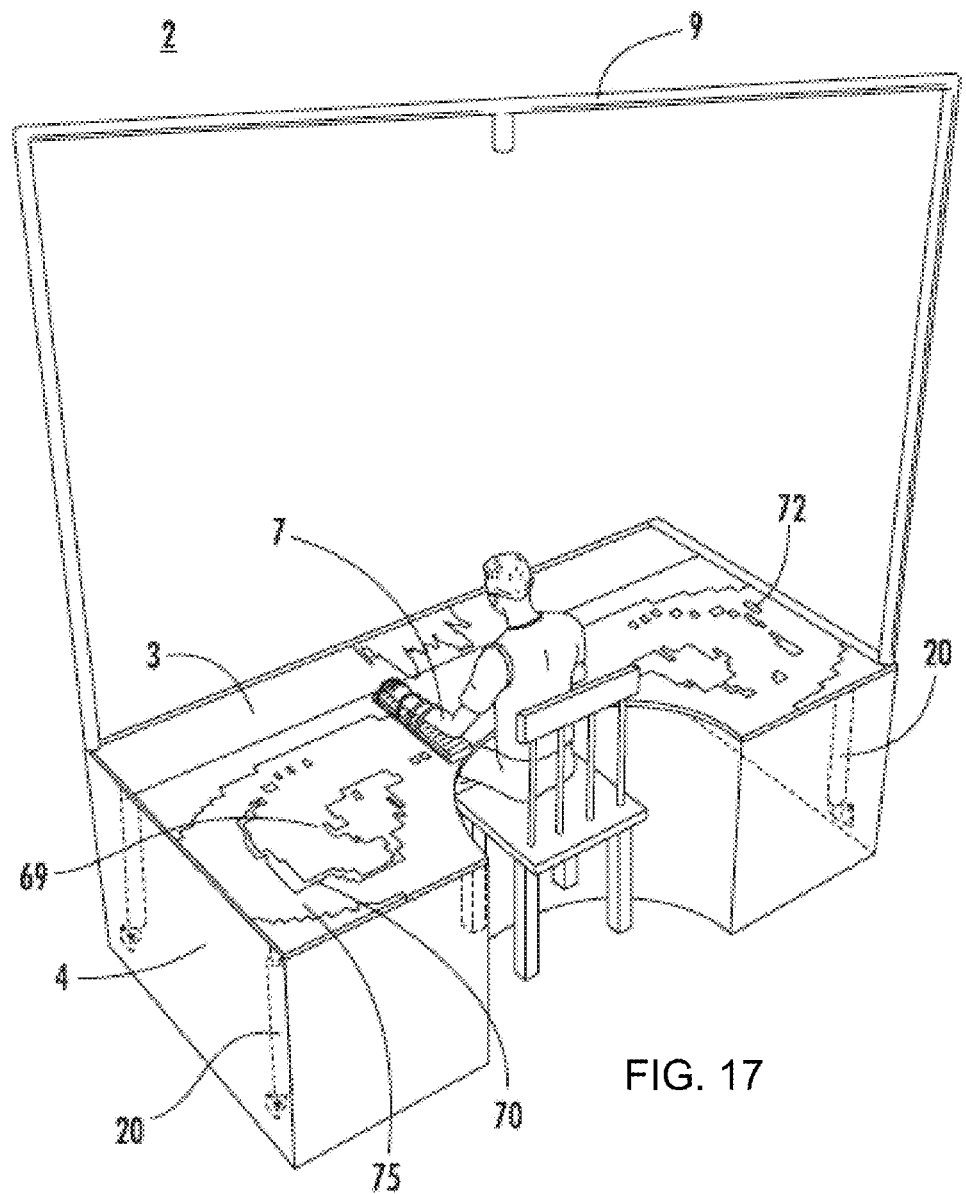

FIG. 17 illustrates an alternate embodiment of tilting table 2. In this embodiment, top surface 3 is also display 69. For example, display 69 can be similar to commercially available thin organic LED (OLED) displays. In this embodiment, the tracking of forearm 7 may be performed by infrared camera 9, or through a touch-sensitive layer 70 incorporated in display 69. In this case the display 69 is a touch sensitive screen such as those available commercially. In case overhead camera 9 is used, forearm support assembly 25 is modified as shown in FIG. 16. Actuator assembly 20 can be connected to frame 72 bordering display 69 and to supporting surface 4. A low-friction transparent film 75 can be retrofitted to display 69, to prevent scratching by the forearm support assemblies 71 and 73 that sit on it.

Figure 18:
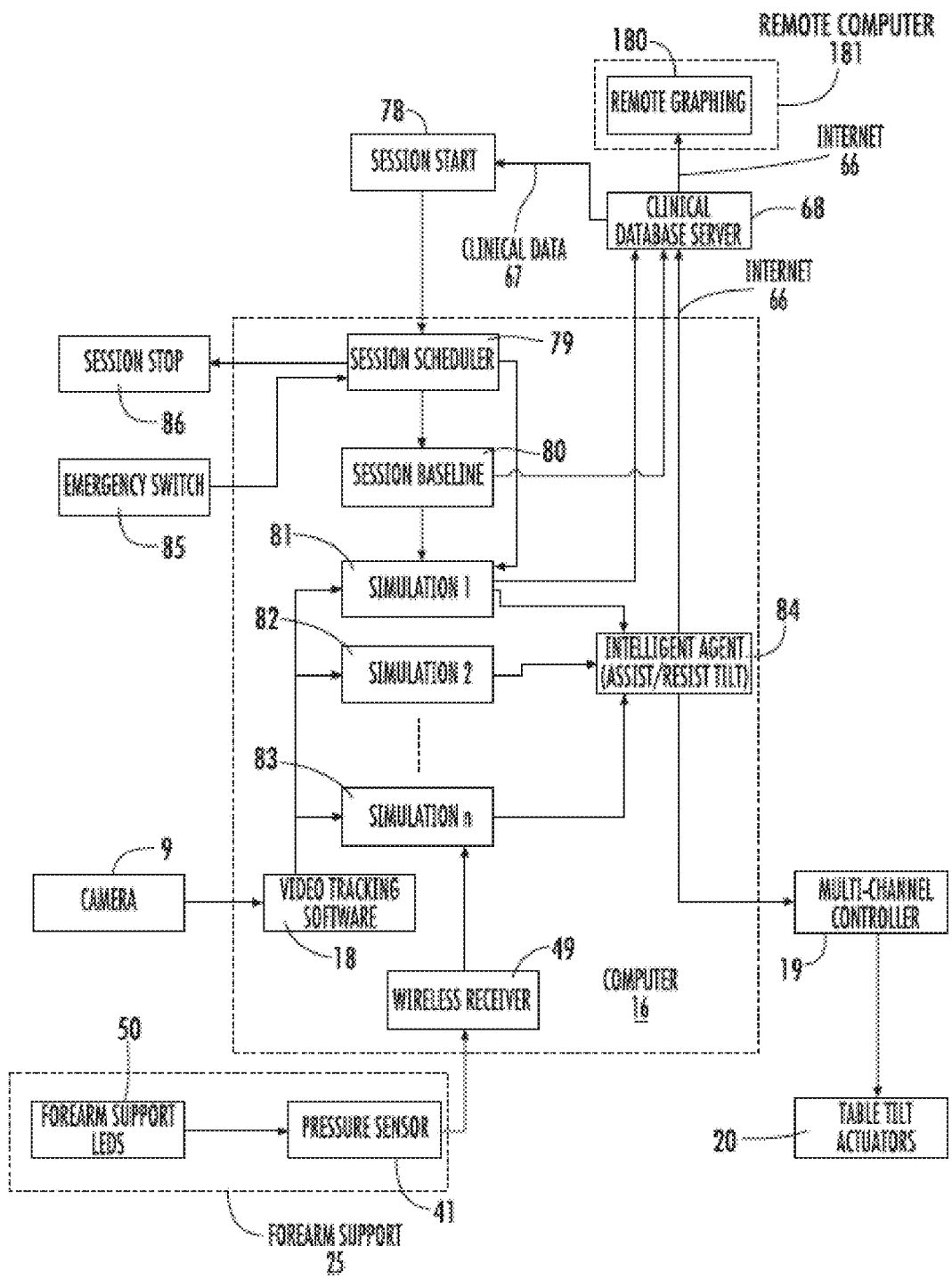

A system block diagram for the tilting rehabilitation table system 1 is illustrated in FIG. 18. Each rehabilitation session starts with session start block 78. Session start block 78 loads the patient's ID and other clinical data 67 for arm 7 to be rehabilitated. Session start block 78 transfers control to the session scheduler block 79 which sets the structure of a rehabilitation session, for example, number, type and order of exercises, as well as the difficulty level settings. Session scheduler block 79 is structured such that it applies a customized treatment depending on progress of patient 5 (the order of the particular session being done out of the prescribed number of sessions). Session scheduler block 79 begins by starting session baseline 80 which measures the performance of patient 5 in that day. Session baseline 80 is stored transparently by clinical database server 68 and can be used to track progress of patient 5 over the sequence of rehabilitation sessions. Patient's 5 progress can be graphed using remote graphing application 180 running on remote computer 181. It is envisioned that remote computer 181 communicates with clinical database server over Internet 66. Session baseline 80 is also used to fine-tune the "gains" of exercise simulation blocks 81, 82 and 83, such that in virtual reality movements are amplified and success assured even for very limited real arm 7 movements. Exercise simulation blocks 81, 82 and 83 can perform exercise simulation 17. Intelligent agent block 84 monitors the patient progress and can automatically vary tilt angle 15 to assist/resist movement. Intelligent agent block 84 can control actuators 20 through their controller 19 connected to computer 16 running exercise simulation blocks 81, 82 and 83. Actuators 20 provide data to exercise simulation blocks 81, 82 and 83 such that virtual table (not shown) in the scene mimics tilt of tilting table 2. Video camera 9 or video cameras 9A and 9B detect(s) the position of LEDs 50 at the top of forearm support assemblies 25 and sends the information to tracking software 18 run by computer 16. Tracking software 18 extracts arm position information and body leaning information and transmits this data to exercise simulation blocks 81, 82 and 83. This data is then used to animate in real time an avatar of the patient's hand(s) (not shown). Manual emergency switch 85, when pressed by attending therapist and/or patient 5 triggers an end to the rehabilitation session through software block 86.

Figure 19:
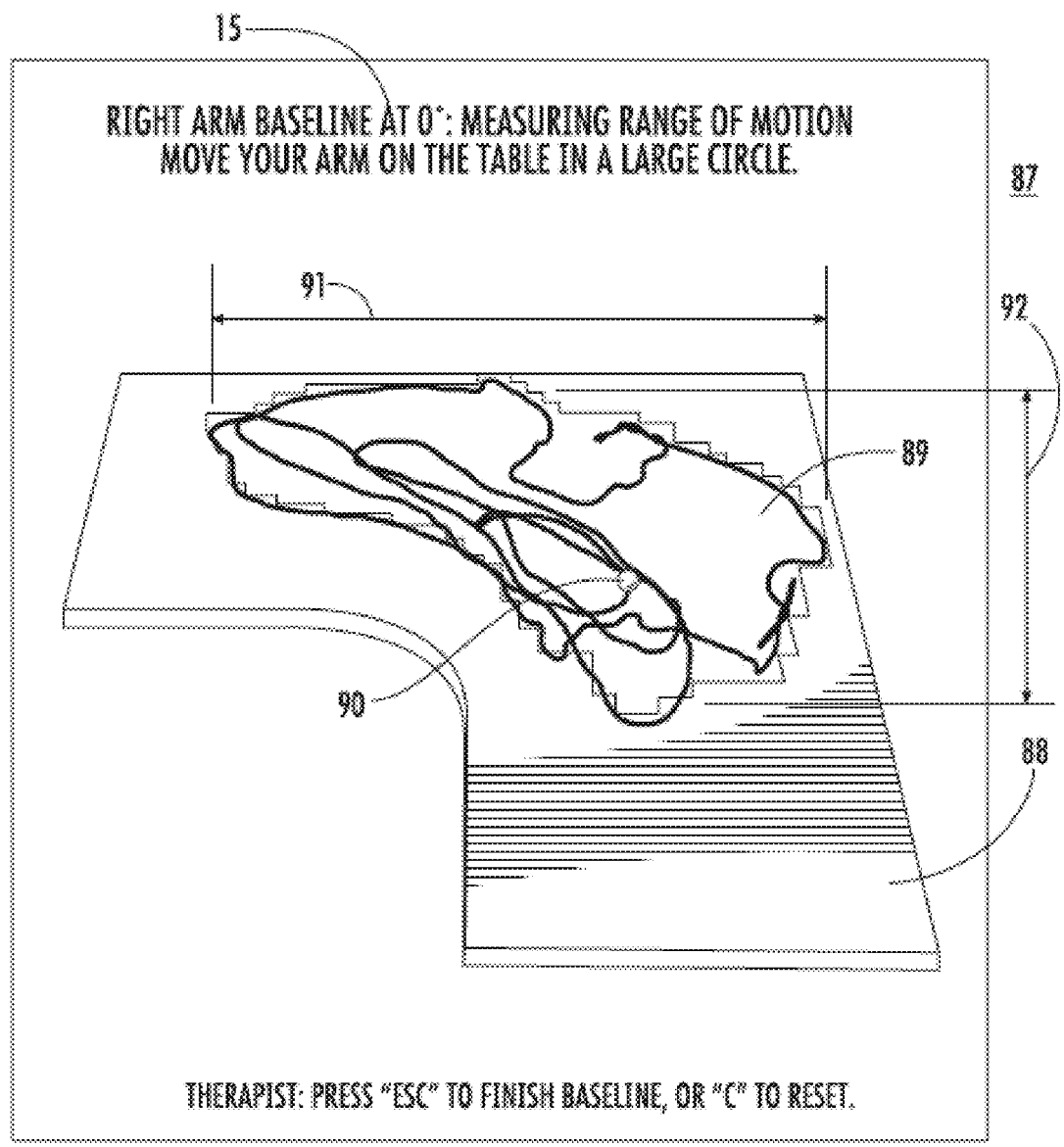

FIG. 19 illustrates an example of patient baseline screen 87 displayed in display 8 or on display 69. Patient 5 is asked to move the arm 7 in large circles to color virtual representation 88 of the rehabilitation table surface 3. The surface of colored area 89 increases with the movement of virtual sphere 90 which responds to the movements of forearm support assembly 25. Size and shape of colored area 89 are a measure of the ability of patient 5 that day. Extent of movement 91 in the left/right (horizontal) direction and extent of movement 92 in the in/out direction are used to adjust the rehabilitation exercise simulation blocks 81, 82 and 83. Baseline screen 87 also shows tilt angle 15 at which baseline 80 was taken. Baseline screen also measures the grasping ability of the patient that day. This is visualized by a thermometer-like display to one side of the virtual table. The stronger the patient squeezes, the higher the vertical line that indicates the maximum squeeze effort. Numerical values, such as those output by the pressure sensor in the forearm support are displayed next to the strength gauge.

Figure 20A:
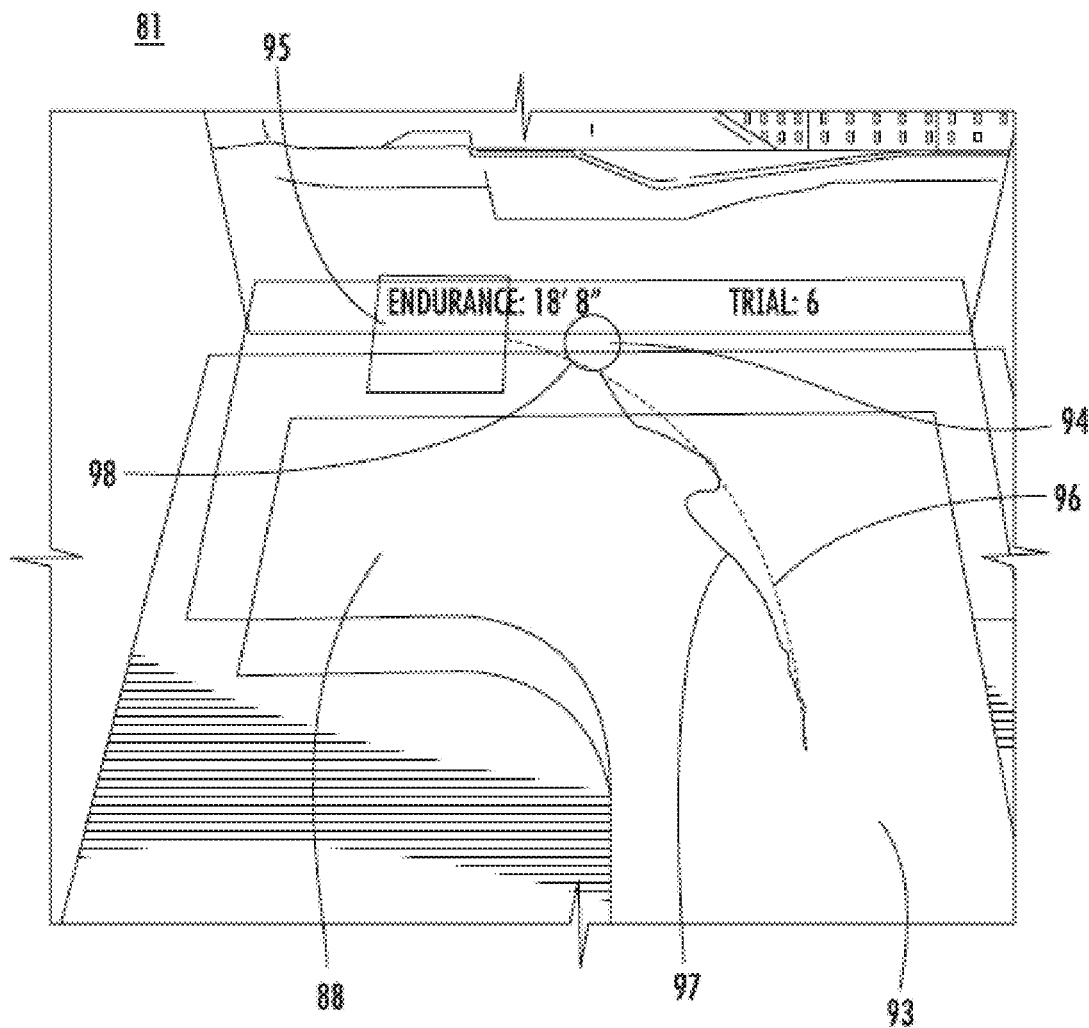

FIG. 20A shows an embodiment of rehabilitation exercise simulation block 81 with a virtual world representation having tilted table avatar 88. Virtual sphere 94 is shown on table surface 93 together with a virtual target rectangle 95. An ideal path between virtual sphere 94 and virtual target rectangle 95 is visualized by path shown as dotted line 96. The placement of virtual target rectangle 95 and virtual sphere 94 on table surface 88 is such that it requires patient 5 to move arm 7 close to extent of movement 91 and extent of movement 92 of baseline 87. Patient 5 is asked to pick up virtual sphere 94 with a semi-transparent hand avatar 98 and place it in virtual target rectangle area 95. In order to grasp virtual sphere 94, transparent hand avatar 98 has to overlap virtual sphere 94 and patient 5 squeezes compliant element 44 on forearm support assembly 25, as shown in FIG. 1. Real movement of patient 5 is tracked by video camera 9 and computer 16 shows a corresponding trace 97 on table surface 88. In one embodiment, if the patient has limited real movement, then the virtual scene is zoomed in to maximize scene detail and thus allowing patient to better control the arm movement to follow prescribed trajectory 96. It is envisioned that the zooming in proportionally shrinks the size of the hand avatar and ball to be manipulated.

Figure 20B:
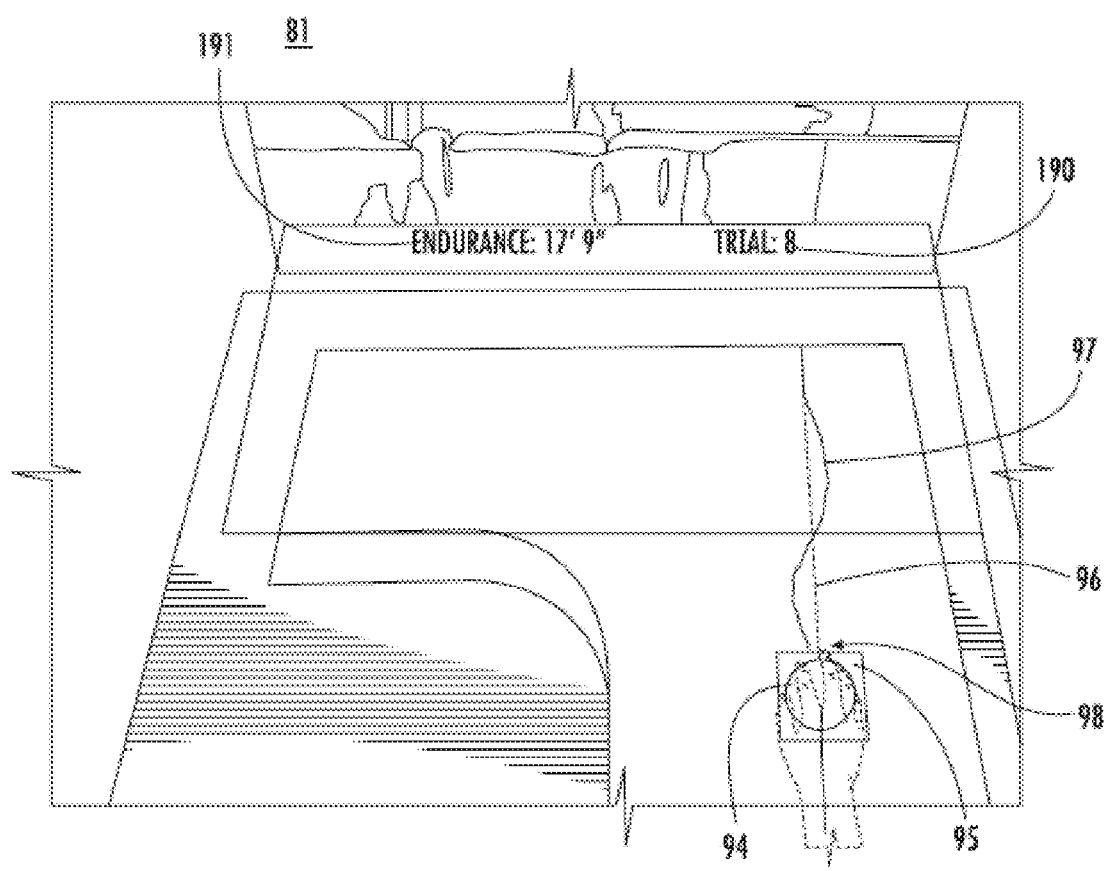

FIG. 20B shows an alternate embodiment of exercise simulation block 81 of the pick-and-place exercise in which ideal path 96 shown as a straight dotted line. This corresponds to in/out (shoulder flexion/extension) movements of arm 7. This process is repeated a number of times, with the trial (repetition) number 190 and the total arm movement (endurance) 191 corresponding to these repetitions being displayed in simulation 81. Other placements of virtual target rectangle 95 and virtual sphere 94 can be used with corresponding ideal path specifications 96. The difficulty exercise simulation block 81 such as a pick-and-place exercise, is varied by making virtual target rectangle 95 smaller and by requiring patient 5 to make more pick-and-place movements. For patient 5 capable of exerting finger forces 45, difficulty is further increased by elevating the threshold of finger grasping forces 45 detected by the forearm assembly 25 in FIG. 8 at which level corresponding hand avatar 98 can capture virtual sphere 94. A further difficulty increase is achieved by requiring that patient 5 maintains grip strength during the pick-and-place trajectory. The necessary threshold at which computer determines continued grasping is a small percentage of maximum voluntary grasp strength measured at baseline. It is known in the art that continuous grasping is more fatiguing, and low thresholds diminish the chance of muscle pain and discomfort for patient 5.

Figure 20C:
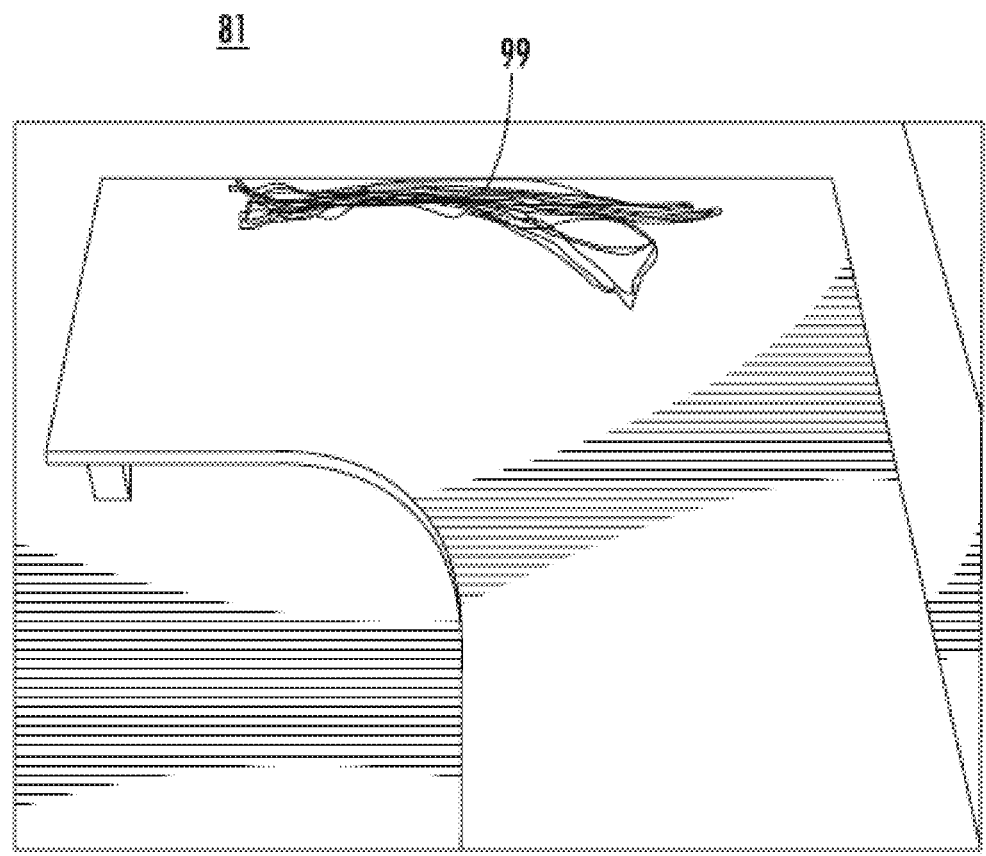

FIG. 20C shows bundle of traces 99 displayed by exercise simulation block 81 at the end of exercises after a number of pick-and-place movements were completed. In this embodiment, bundle of traces 99 corresponds to repeated pick-and-place movements of arm 7 in the left-right-left (shoulder abduction/adduction) direction. The tightness of bundle of traces 99 is indicative of the motor control abilities that day for patient 5.

Figure 21A:
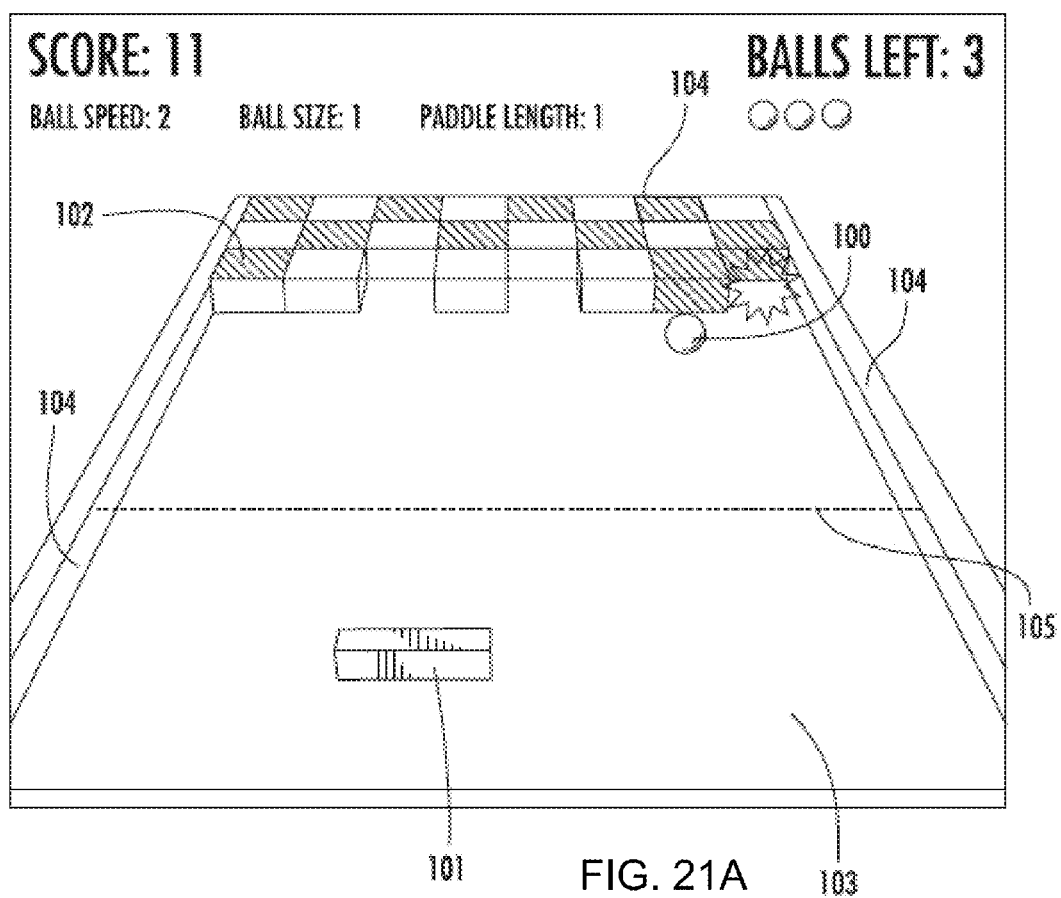

FIG. 21A shows an embodiment of exercise simulation block 82 referred to "Breakout 3D" game. This exercise depicts ball 100, paddle 101, and array of cubes 102, all located on play board 103. Paddle 101 is used to bounce ball 100 towards cubes 102 with one cube being destroyed for each bounce of ball 100 off of paddle 101. Ball 100 can bounce off of three sides 104 of play board 103, or off multiple cubes 102, but is lost if it misses paddle 101. In an alternate embodiment, paddle 101 can move mostly left-right, within the lower portion of play board 103, delineated by dashed line 105. The difficulty of exercise simulation block 82 is set by the number of available balls 100, the speed of balls 100, and the size of paddle 101. The higher the speed of ball 100, the smaller the size of paddle 101, and the fewer the number of available balls 100, the harder the Breakout 3D game of exercise simulation block 82 is. The goal of the Breakout 3D exercise simulation block 82 is to destroy all cubes 102 with the available number of balls 100. The Breakout 3D of exercise simulation block 82 is designed to improve hand-eye coordination, speed of arm movement, cognitive anticipatory strategies, and focusing of patient 5.

Figure 21B:
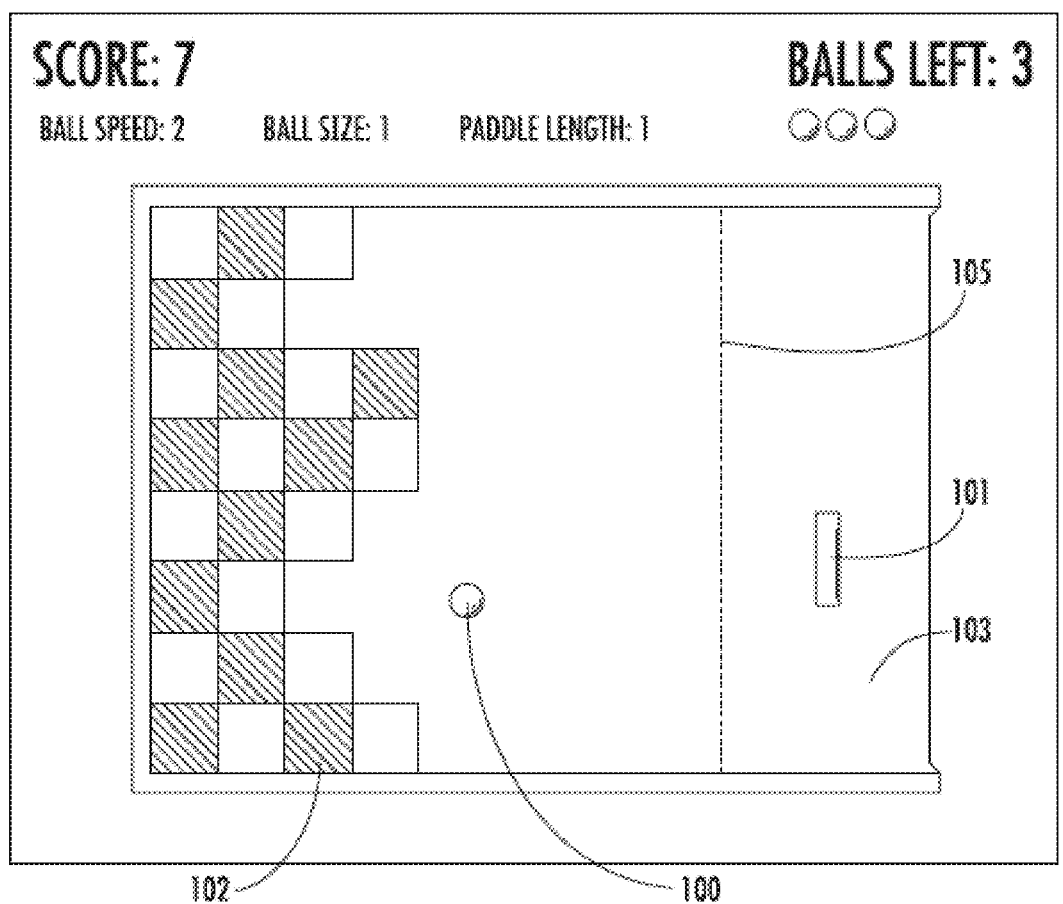

FIG. 21B is another embodiment of the Breakout 3D of exercise simulation block 82, in which board 103 is rotated to show array of cubes 102 to one side of the scene. In this example paddle 101 moves mostly vertically in the scene, within the area to the right of dotted line 105, requiring corresponding in-out-in movements (shoulder flexion/extension) of arm 7. It is further envisioned that at higher levels of difficulty patient 5 needs to grasp above threshold for the ball 100 to bounce off paddle 101, else the ball will be passing through the paddle and be lost. This Breakout 3D game implements dual-tasking rehabilitation, a term known in the art, but associated mostly with walking and talking in the elderly.

Figure 22:
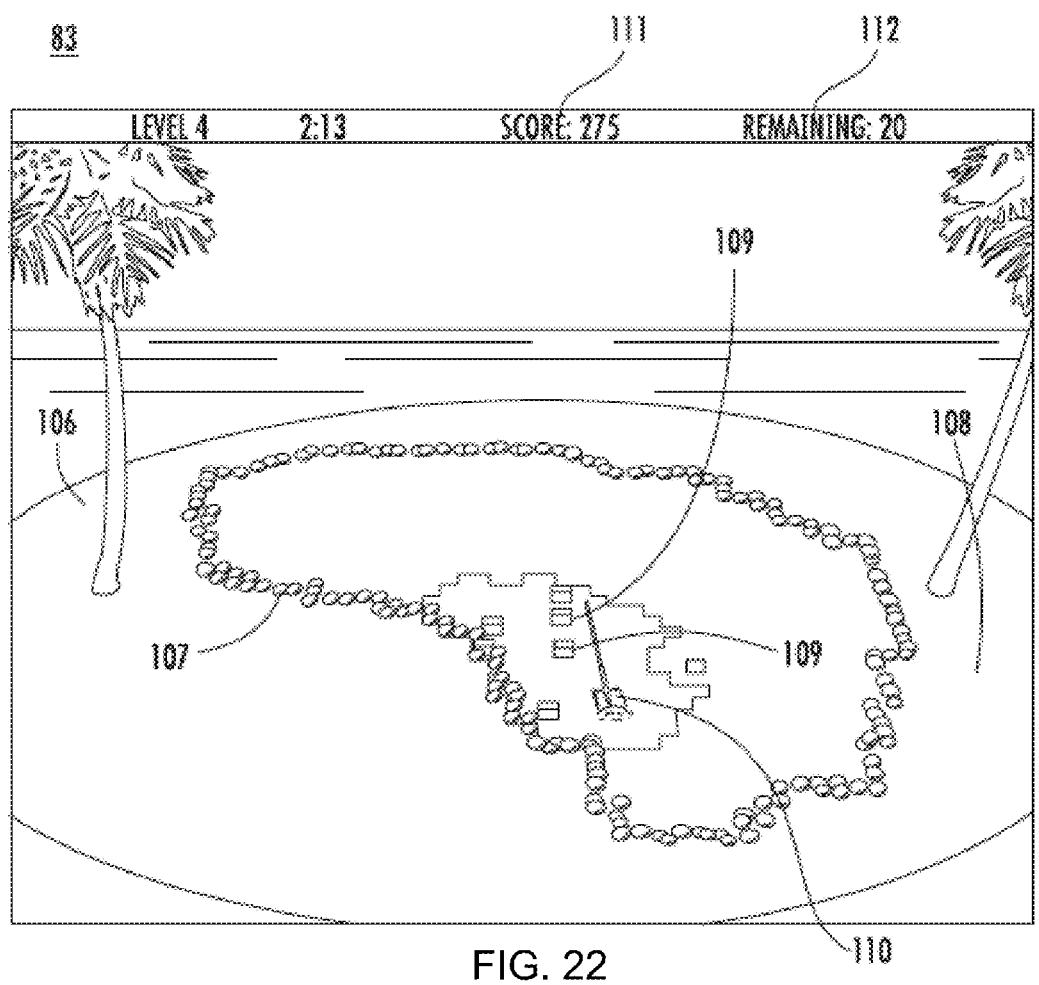

FIG. 22 is an embodiment of exercise simulation block 83 called "Treasure Hunt". The scene depicts deserted island 106 with line of stones 107 on top of virtual sand 108. The shape of line of stones 107 replicates the shape of baseline surface colored area 89. There are a number of virtual treasures chests 109 inside sand 108 surrounded by line of stones 107. Patient 5 controls virtual shovel 110 with which to remove sand 108 covering treasure chests 109. Every time a new treasure chest 109 is found score 111 displayed in the scene is increased. In order to find a new treasure chest 109 shovel 110 has to be moved in sand 108 that overlaps treasure chest 109. If tracking software 18 detects leaning of patient 5 treasure chest 109 is not revealed even if shovel 110 is in the correct position and score 111 is not increased. At higher level of difficulty, a sand storm occurs. Part of the already uncovered treasure chests 109 are covered again by sand 108 requiring more movement of arm 7 of patient 5 to uncover treasure chest 109 again. The Treasure Hunt exercise simulation block 83 is timed and remaining time 112 is displayed at the top of the scene. Patient 5 attempts to uncover all of treasure chests 109 in the allowed amount of time 112. This exercise is aimed at increasing arm endurance of patient 5. In other embodiments, other simulation exercises can be played by patient 5.

In an experimental therapy, two patients in the chronic stage post severe TBI participated in a feasibility study of convergent therapy to determine patient acceptance and perceived clinical benefit. They practiced the affected upper extremity playing custom video games on an experimental system which incorporated the tilting table described above. They underwent 18 sessions over 6 weeks, as well as 3 motor and neuro-psychological evaluations pre-, post- and at 6 weeks follow up. The exercises were gradated in difficulty, included multiple dual-tasks, and rewarded the participants for good performance. In both cases, there were improvements in focusing and executive function. One patient also showed improved visual memory and a decline in depression from pre-treatment to post-treatment and maintained these gains at follow-up. In the motor domain, both clients increased their shoulder strength and were faster on the Jebsen test of hand function. Both demonstrated improvement in activities of daily living as well. The patients liked the technology and were very motivated. They practiced intensely without a therapist being present.

Figure 23:
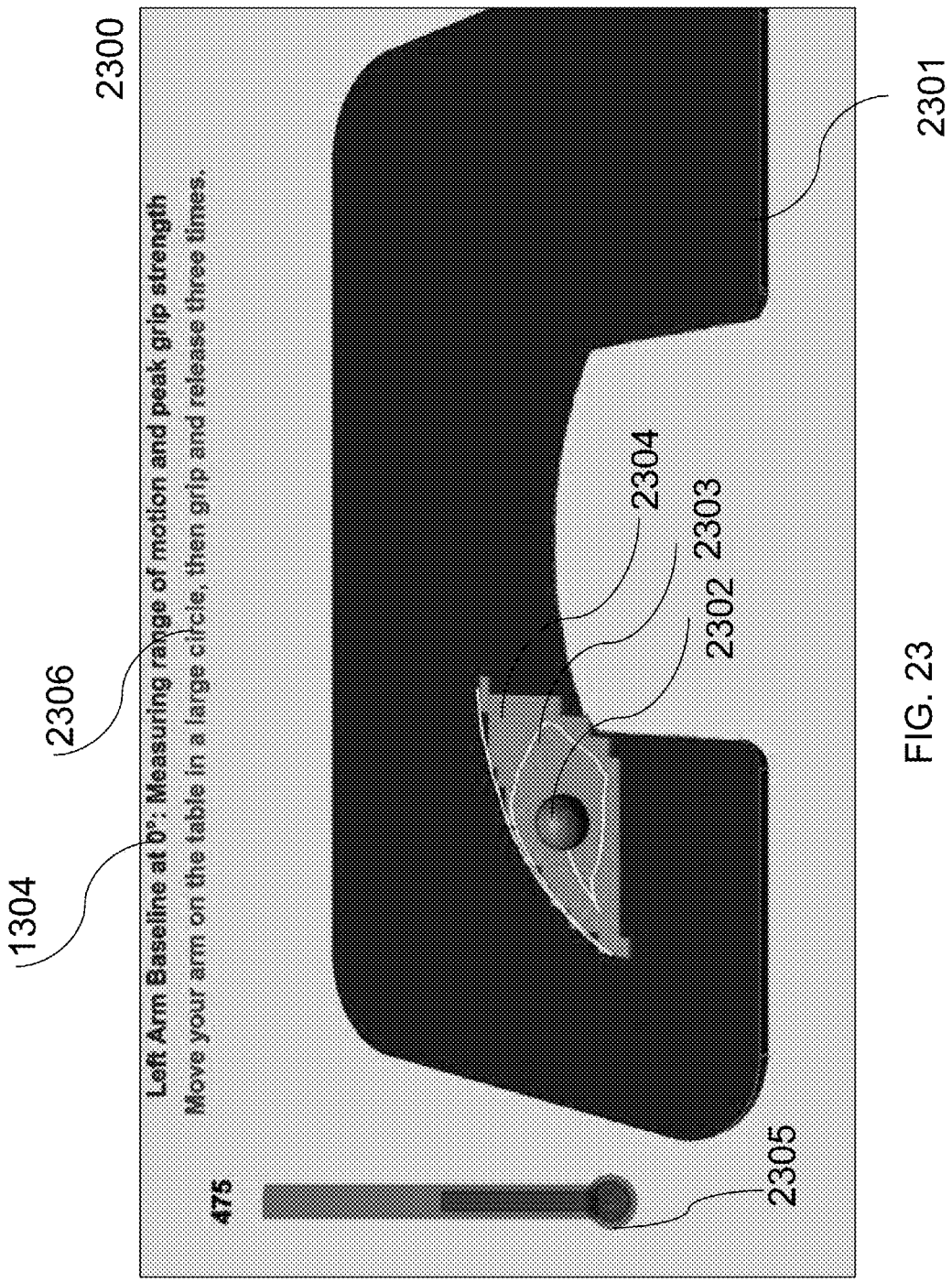
FIGS. 23 and 24 illustrate a display in accordance with an aspect of the present invention.

FIG. 23 illustrates a base screen 2300 for a patient in accordance with an aspect of the present invention. It shows a table top 2301 with an avatar ball 2302 that represents an actual squeeze ball or input device that can be squeezed by the patient. A drawn path 2303 shows a path that is followed by the hand of the patient with the ball. A patch 2304 shows a reach of a patient's arm (in this case the left arm). In a further embodiment, the table supports the patient's arm, and the area the patient can reach is colored in a lighter shade. The reachable area is dependent of title angle 1304 displayed on the screen. Results of an exercise can be provided as feedback. For instance a thermometer-like bar 2305 can provide the level of force that a patient creates by squeezing the input device that may be a squeeze ball. Instructions 2306 and/or explanation to a patient can be provided on the screen 2300. The force thermometer bar 2305 can be placed inside a game screen to give additional feedback to the patient. It is appreciated that such grasping force feedback is useful for patients who have lost their sense of touch due to, for example stroke, and helps patients know how hard they squeeze the sensing element.

Figure 24:
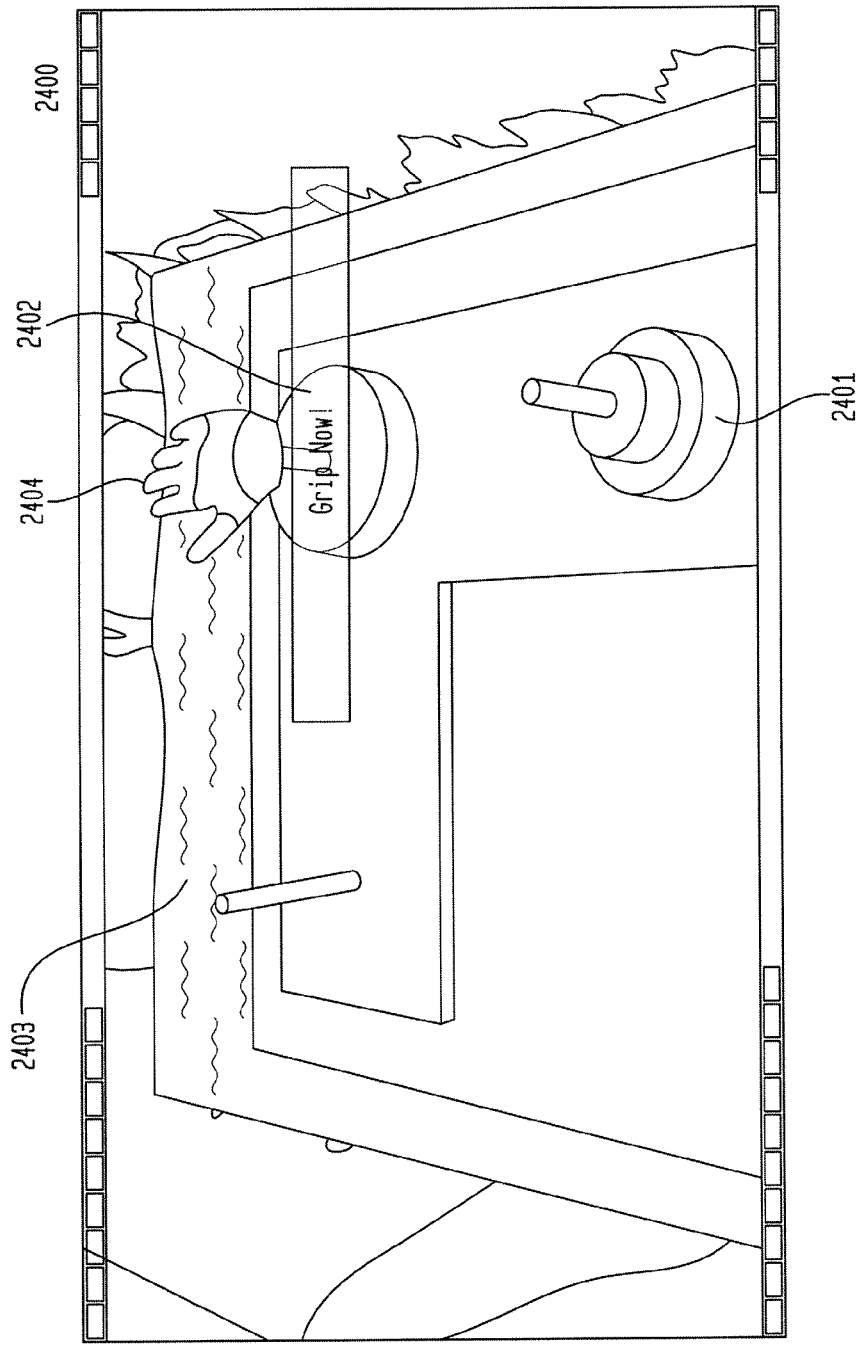

FIG. 24 shows, as an illustrative example, a screen 2400 of a game in accordance with an aspect of the present invention. The displayed game is the known game of Tower of Hanoi 3D wherein a tower of disks in different sizes stacked on a first pin 2401 has to be moved to a second pin for instance 2403 wherein only one disk is allowed to be moved at a time and no disk of greater diameter is allowed to sit on a disk of smaller diameter. Three pins 2401, 2402 and 2403 are available, allowing a gamer to make intermediate steps to prevent placing disks at the wrong order. The disks are manipulated by the patient using an input device that controls an avatar hand 2404. Instructions to take action may appear on the screen. The patient needs for instance to squeeze a deformable ball on arm support to grasp a disk with the hand avatar on the screen and to move the disk to a different pin. The patient needs to maintain grasp en route to another pin or the disk may fall out of the avatar's hand. The screen 2400 shows just one configuration of the exercise for this game. One may increase or decrease the difficulty of the game by changing positions of the pins, by changing the number of disks that need to be stacked, by changing the sizes of the disks, by changing the sizes of the holes of the disks and the tolerance of such holes compared to the pins and by changing the shapes of the pins, and by any other configuration that will change the difficulty of doing the game. FIG. 25 illustrates a tilting table 2501 in accordance with an aspect of the present invention. In one embodiment the table 2501 uses 4 actuators only, and that the table tilts up or down, lifts up/down, is accessible by wheelchair (without transfer), and has an underside safety plate 2502.

The plate 2502 has a switch that stops table movement if contact is detected with patient's legs. For example, the plate 2502 may come in contact with a patient's leg, pushing the plate 2502 toward the table and closing (or opening) a switch. The switch controls operation of a motor which stops the movement of the tilt table when the plate 2502 contacts a patient's leg. A right arm input device 2503 is also provided in FIG. 25.

Figure 26:
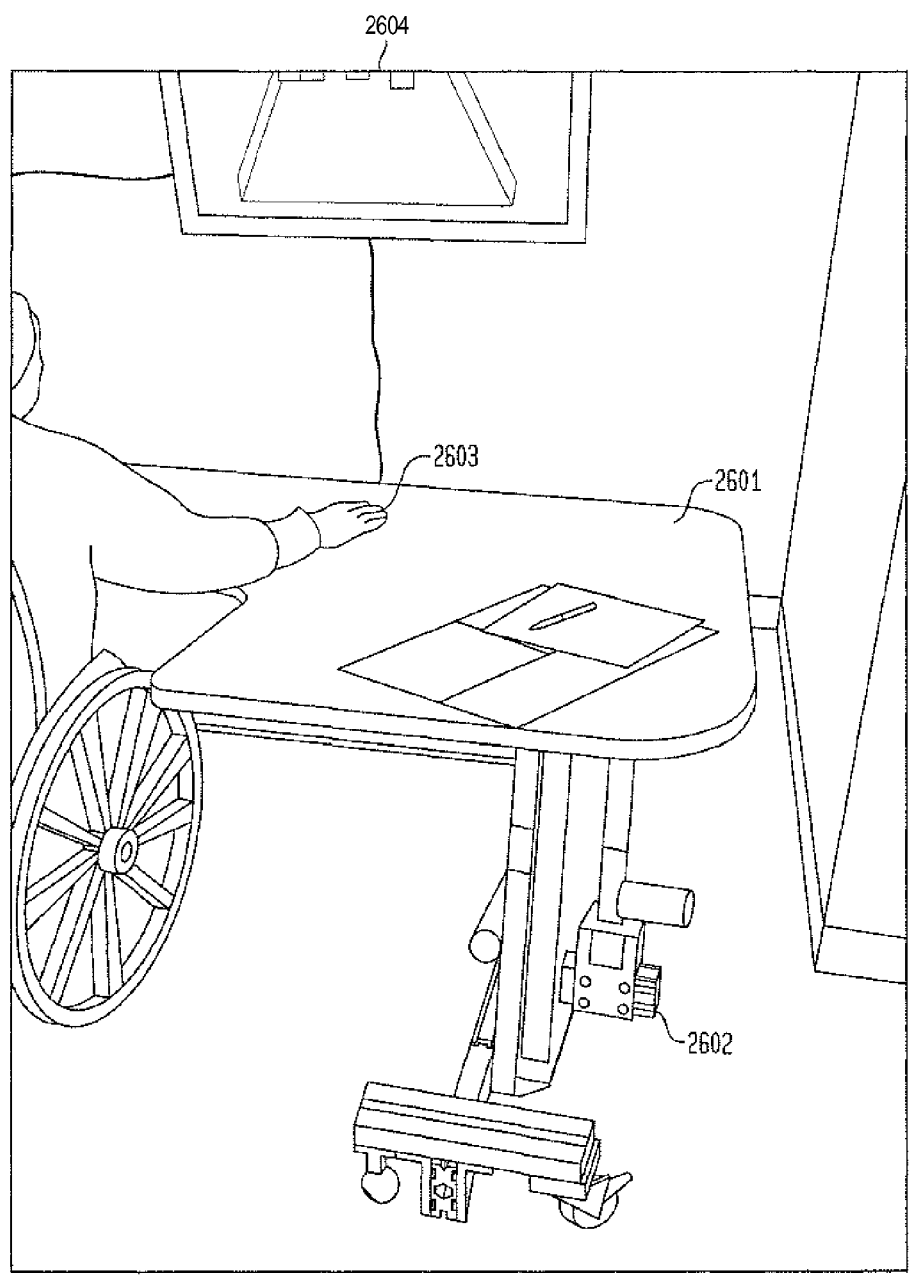

FIG. 26 is a further illustration of a tilt table 2601 which has a tilt mechanism 2602. A game display 2604 and input device 2603 are also shown.

It is to be understood that the above described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

The invention claimed is:

1. A method of providing cognitive and physical rehabilitation to a patient with a computer, comprising:
    having the patient play a virtual reality game through an avatar that simultaneously elicits cognitive mental effort and physical exertion on a limb of the patient, operating on a computerized non-portable system or on single portable device;
    measuring cognitive responses of the patient by measuring results of the patient playing the virtual reality game, wherein the measured cognitive responses includes measurements of reaction speed, short term memory, long term memory, pairing memory, focusing and executive function;
    measuring motor responses of the patient with one or more devices while the patient plays the virtual reality game and reporting the motor response to the computer, wherein the measured motor responses include limb strength, limb speed, limb range of movement, motor control, endurance, hand-eye coordination, and dual-tasking;
    the computer reporting the measured cognitive responses and the measured motor responses through a network to a server that stores the measured cognitive responses and the measured motor responses;
    reviewing the measured cognitive responses and the measured motor responses and adjusting the virtual reality game difficulty or the virtual reality game according to whether the patient is progressing in the cognitive and physical rehabilitation;
    a first medical services provider accessing the measured cognitive responses of the patient by accessing the server over the network;
    a second medical services provider accessing the measured motor responses of the patient by accessing the server over the network; and
    the first medical services provider and the second medical services provider providing instructions to the computer based on the measured cognitive responses and the measured motor responses of the patient.

2. The method of claim 1, comprising repeating the steps of claim 1 with the computer directing the patient in accordance with the instructions from the first and second medical services providers.

3. The method of claim 1, comprising the computer analyzing the cognitive responses and the measured motor responses and providing feedback to the patient.

4. The method of claim 1, wherein the one or more devices is selected from the group consisting of: one or more cameras, one or more accelerometers, one or more weights, one or more dynamometers, one or more timers, one or more counters, one or more goniometers, one or more tilt tables and combinations thereof.

5. The method of claim 1, wherein the network is the Internet to mediate cloud rehabilitation.

6. A system for providing simultaneous cognitive and physical rehabilitation to a patient with a computer, comprising:
    a computer that provides instructions to the patient to play a virtual reality game through an avatar;
    a first set of one or more devices that measure cognitive responses of the patient that are connected to the computer and that report the measured cognitive responses to the computer, wherein the measured cognitive responses includes measurements of reaction speed, short term memory, long term memory, pairing memory, focusing, and executive function;
    a second set of one or more devices that measure motor responses of the patient that are connected to the computer and that report the measured motor responses to the computer, wherein the measured motor responses include limb strength, limb speed, limb range of movement, motor control, endurance, hand-eye coordination, and dual-tasking;
    wherein the computer sends the measured cognitive responses and the measured motor responses over a network to a server that stores the measured cognitive responses and the measured motor responses; and
    the computer reviews the measured cognitive responses and the measured motor responses and adjusts the virtual reality game difficulty or the virtual reality game according to whether the patient is progressing in the cognitive and physical rehabilitation;

a second computer connected to the network, wherein a first medical services provider uses the second computer to access the measured cognitive responses of the patient by accessing the server over the network;

a third computer connected to the network, wherein a second medical services provider uses the third computer to access the measured motor responses of the patient by accessing the server over the network; and wherein the first medical services provider provides instructions to the computer over the network and through the server based on the measured cognitive responses and wherein the second medical service provider provides instructions to the computer over the network and through the server based on the measured motor responses of the patient.

7. The system of claim 6, wherein the computer provides new instructions to the patient based on the instructions from the first and second medical services providers.

8. The system of claim 6, wherein the computer analyzes the cognitive response and the measured motor responses and provides feedback to the patient.

9. The system of claim 6, wherein the one or more devices is selected from the group consisting of: one or more cameras, one or more accelerometers, one or more weights, one or more dynamometers, one or more timers, one or more counters, one or more goniometers, one or more tilt tables and combinations thereof.

10. The system of claim 6, wherein the network is the Internet.

* * * * *